US010668077B2

(12) United States Patent
Shuttleworth et al.

(10) Patent No.: US 10,668,077 B2
(45) Date of Patent: Jun. 2, 2020

(54) COMPOSITIONS COMPRISING PHOSPHOINOSITIDE 3-KINASE INHIBITORS AND A SECOND ANTIPROLIFERATIVE AGENT

(71) Applicant: Karus Therapeutics Limited, Oxfordshire (GB)

(72) Inventors: Stephen Joseph Shuttleworth, Oxfordshire (GB); Andrew David Whale, Oxfordshire (GB)

(73) Assignee: Karus Therapeutics Limited, Oxfordshire (GB)

( * ) Notice: Subject to any disclaimer, the term of this patent is extended or adjusted under 35 U.S.C. 154(b) by 0 days.

(21) Appl. No.: 15/753,353

(22) PCT Filed: Aug. 19, 2016

(86) PCT No.: PCT/GB2016/052575
§ 371 (c)(1),
(2) Date: Feb. 19, 2018

(87) PCT Pub. No.: WO2017/029517
PCT Pub. Date: Feb. 23, 2017

(65) Prior Publication Data
US 2018/0243313 A1    Aug. 30, 2018

(30) Foreign Application Priority Data

Aug. 19, 2015 (GB) .................................. 1514760.6

(51) Int. Cl.
| C07D 471/14 | (2006.01) |
| A61K 31/5377 | (2006.01) |
| A61K 31/4184 | (2006.01) |
| A61K 31/519 | (2006.01) |
| A61K 31/5386 | (2006.01) |
| A61K 31/69 | (2006.01) |
| A61K 45/06 | (2006.01) |
| A61K 38/05 | (2006.01) |

(52) U.S. Cl.
CPC ...... *A61K 31/5377* (2013.01); *A61K 31/4184* (2013.01); *A61K 31/519* (2013.01); *A61K 31/5386* (2013.01); *A61K 31/69* (2013.01); *A61K 38/05* (2013.01); *A61K 45/06* (2013.01)

(58) Field of Classification Search
CPC ............ C07D 491/147; C07D 471/14; C07D 491/14; C07D 495/14; A61K 31/5377; A61K 31/4184; A61K 31/519; A61K 31/5386; A61K 31/69; A61K 38/05; A61K 45/06
See application file for complete search history.

(56) References Cited

U.S. PATENT DOCUMENTS

| 3,491,092 A | 1/1970 | Grigat et al. |
| 4,017,500 A | 4/1977 | Mayer et al. |
| 5,703,075 A | 12/1997 | Gammill et al. |
| 7,361,662 B2 | 4/2008 | Rault et al. |
| 8,981,087 B2 | 3/2015 | Shuttleworth et al. |
| 9,200,007 B2* | 12/2015 | Shuttleworth ..... C07D 491/147 |
| 9,266,879 B2 | 2/2016 | Shuttleworth et al. |
| 9,580,442 B2* | 2/2017 | Shuttleworth ....... C07D 519/00 |
| 9,663,487 B2 | 5/2017 | Shuttleworth et al. |
| 9,938,290 B2* | 4/2018 | Shuttleworth ..... C07D 491/147 |
| 9,981,987 B2* | 5/2018 | Shuttleworth ....... C07D 519/00 |
| 10,035,785 B2 | 7/2018 | Shuttleworth et al. |
| 10,377,764 B2* | 8/2019 | Shuttleworth ....... C07D 519/00 |
| 10,442,815 B2* | 10/2019 | Shuttleworth ....... C07D 495/14 |
| 10,501,478 B2* | 12/2019 | Shuttleworth ..... C07D 491/147 |
| 2002/0151544 A1 | 10/2002 | Hayakawa et al. |
| 2007/0135466 A1 | 6/2007 | Ledeboer et al. |
| 2011/0201608 A1 | 8/2011 | Hoffmann et al. |
| 2012/0178737 A1* | 7/2012 | Shuttleworth ....... C07D 495/14 514/210.21 |
| 2013/0109688 A1 | 5/2013 | Shuttleworth et al. |
| 2015/0080395 A1 | 3/2015 | Shuttleworth et al. |
| 2016/0108057 A1* | 4/2016 | Shuttleworth ..... C07D 491/147 514/210.21 |
| 2016/0113932 A1* | 4/2016 | Stern .................. C07K 16/2887 424/133.1 |
| 2016/0347771 A1* | 12/2016 | Shuttleworth ....... C07D 491/14 |

(Continued)

FOREIGN PATENT DOCUMENTS

| EP | 1277738 A1 | 1/2003 |
| EP | 1724267 A1 | 11/2006 |

(Continued)

OTHER PUBLICATIONS

Q. Liu et al., 6 Drug Discovery Today: Therapeutic Strategies, 47-55 (2009) (Year: 2009).*
S.J. Shutteworth et al., 18 Current Medicinal Chemistry, 2686-2714 (2011) (Year: 2011).*
S. Brachmann et al., 21 Current Opinion in Cell Biology, 194-198 (2009) (Year: 2009).*
X. Zhao et al., 23 Bioorganic & Medicinal Chemistry, 891-901 (2015) (Year: 2015).*
Alvarez-Rua et al., "Multiple Hydrogen Bonds and Tautomerism in Naphthyridine Derivatives", New J. Chem. 28, 700-07 (2004).

(Continued)

*Primary Examiner* — Alexander R Pagano
(74) *Attorney, Agent, or Firm* — Goodwin Procter LLP

(57) ABSTRACT

The invention relates to a pharmaceutical composition comprising a combination of a compound of formula (I) or a pharmaceutically acceptable salt thereof, and at least one second agent selected from the group consisting of signal transduction pathway inhibitors, tumour immunotherapeutics, agents inhibiting the BCL2 family of proteins, agents inhibiting Mcl-1, proteasome Inhibitors, poly (ADP-ribose) polymerase (PARP) Inhibitors, aromatase inhibitors, conventional cytotoxic agents or a miscellaneous agent selected from abiraterone, ARN-509 and MYC inhibitors.

17 Claims, No Drawings

(56) References Cited

U.S. PATENT DOCUMENTS

| | | | | |
|---|---|---|---|---|
| 2018/0009826 A1* | 1/2018 | Shuttleworth | ....... | C07D 519/00 |
| 2018/0235974 A1* | 8/2018 | Shuttleworth | ....... | A61K 9/2054 |
| 2018/0243313 A1* | 8/2018 | Shuttleworth | ......... | A61K 45/06 |
| 2018/0243317 A1* | 8/2018 | Shuttleworth | ....... | A61K 31/444 |
| 2018/0244685 A1* | 8/2018 | Shuttleworth | ..... | C07D 491/147 |
| 2018/0244686 A1* | 8/2018 | Shuttleworth | ..... | C07D 491/147 |
| 2019/0040079 A1* | 2/2019 | Shuttleworth | ....... | C07D 495/14 |
| 2019/0092790 A1* | 3/2019 | Shuttleworth | ....... | C07D 519/00 |

FOREIGN PATENT DOCUMENTS

| | | | | |
|---|---|---|---|---|
| GB | 1402431 A * | 8/1975 | ............ | B29D 30/32 |
| WO | WO-01/83456 A1 | 11/2001 | | |
| WO | WO-02/02551 A1 | 1/2002 | | |
| WO | WO-02/085400 A1 | 10/2002 | | |
| WO | WO-2004/006846 A2 | 1/2004 | | |
| WO | WO-2004/043956 A1 | 5/2004 | | |
| WO | WO-2006/046035 A1 | 5/2006 | | |
| WO | WO-2006/127587 A1 | 11/2006 | | |
| WO | WO-2007/084667 A2 | 7/2007 | | |
| WO | WO-2007/122410 A1 | 11/2007 | | |
| WO | WO-2007/127183 A1 | 11/2007 | | |
| WO | WO-2008/064018 A1 | 5/2008 | | |
| WO | WO-2008/094992 A2 | 8/2008 | | |
| WO | WO-2008/121257 A1 | 10/2008 | | |
| WO | WO-2008/145688 A2 | 12/2008 | | |
| WO | WO-2008/150827 A1 | 12/2008 | | |
| WO | WO-2010/015520 A1 | 2/2010 | | |
| WO | WO-2010/037765 A2 | 4/2010 | | |
| WO | WO-2010/052569 A2 | 5/2010 | | |
| WO | WO-2011/012883 A1 | 2/2011 | | |
| WO | WO-2011/021038 A1 | 2/2011 | | |
| WO | WO-2011/079231 A1 | 6/2011 | | |
| WO | WO-2011/135351 A1 | 11/2011 | | |
| WO | WO-2013/014448 A1 | 1/2013 | | |
| WO | WO-2013/017480 A1 | 2/2013 | | |
| WO | WO-2013/132270 A1 | 9/2013 | | |
| WO | WO-2014/081718 A1 | 5/2014 | | |
| WO | WO-2014/181137 A1 | 11/2014 | | |
| WO | WO-2014/210354 A1 | 12/2014 | | |
| WO | WO-2015/054355 A1 | 4/2015 | | |
| WO | WO-2015/121657 A1 | 8/2015 | | |
| WO | WO-2015121657 A1 * | 8/2015 | ........... | C07D 491/14 |
| WO | WO-2017/029514 A1 | 2/2017 | | |
| WO | WO-2017/029517 A1 | 2/2017 | | |
| WO | WO-2017/029518 A1 | 2/2017 | | |
| WO | WO-2017/029519 A1 | 2/2017 | | |
| WO | WO-2017/029521 A1 | 2/2017 | | |

OTHER PUBLICATIONS

Ameriks et al., "Small Molecule Inhibitors of Phosphoinositide 3-Kinase (PI3K) δ and γ", Current Topics in Medicinal Chemistry, 2009, vol. 9, No. 8, pp. 738-753.
Baldev Singh et al., "Novel cAMP PDE III Inhibitors: 1,6-Naphthyridin-2(18)-ones", Journal of Medicinal Chemistry, American Chemical Society, 35(26): 5858-4865, Jan. 1, 1992, New York. CAS Registry Nos. 1214438-02-4 and 1214393-37-9 (Mar. 25, 2010).
D.A. Kovalskiy et al., "Synthesis of 7-(3-piperidyl)[1,6]naphthyridine and 7-(4-piperidyl)[1,6]naphthyridine", Chemistry of Heterocyclic Compounds, 45(9): 1053-1057, Nov. 24, 2009.
Database Chemcats [Online], Chemical Abstracts Service, Apr. 22, 2011, Columbus, Ohio.
Erik L. Meredith et al., "Identification of Orally Available Naphthyridine Protein Kinase D Inhibitors", Journal of Medicinal Chemistry, 53(15): 5400-5421, Aug. 12, 2010.
Fabbro et al. Pharmacology & Therapeutics 93, 79-98, 2002.
Golub et al., Science, 286, 531-537, 1999.
Hayakawa, et al., "Synthesis and Biological Evaluation of Pyrido[3',2':4,5]furo[3,2-d]pyrimidine Derivatives as Novel PI3 Kinase p110α Inhibitors" Bioorganic & Medicinal Chemistry Letters, 2007, vol. 17, pp. 2438-2442.

Hollebecque A et al., (2014), 'A Phase Ib Trial of LY2584702 Tosylate, a p70 S6 Inhibitor, in Combination with Erlotinib or Everolimus in Patients with Solid Tumours,' Eur J Cancer, 50(5):876-84.
International Preliminary Report on Patentability and Written Opinion of the International Searching Authority for PCT/GB2010/051221 dated Jan. 31, 2012 (7 pages).
International Preliminary Report on Patentability and Written Opinion of the International Searching Authority for PCT/GB2010/051370 dated Feb. 21, 2012 (6 pages).
International Preliminary Report on Patentability and Written Opinion of the International Searching Authority for PCT/GB2011/050824 dated Nov. 6, 2012 (7 pages).
International Preliminary Report on Patentability and Written Opinion of the International Searching Authority for PCT/GB2013/050583 dated Sep. 9, 2014 (6 pages).
International Search Report of the International Searching Authority for PCT/GB2010/051221 dated Oct. 7, 2010 (4 pages).
International Search Report of the International Searching Authority for PCT/GB2010/051370 dated Nov. 9, 2010 (4 pages).
International Search Report of the International Searching Authority for PCT/GB2011/050824 dated Jul. 12, 2011 (5 pages).
International Search Report of the International Searching Authority for PCT/GB2013/050583 dated May 6, 2013 (4 pages).
Lin L et al., (2014), 'Dual Targeting of Glioblastoma Multiforme with a Proteasome Inhibitor (Velcade) and a Phosphatidylinositol 3-Kinase Inhibitor (ZSTK474),' Int J Oncol, 44(2):557-62.
Mass, R. D., Int. J. Radiation Oncology Bio. Phys. vol. 58 (3): 932-940, 2004.
Notification of the Transmittal of the International Search Report and the Written Opinion of the International Searching Authority, or the Declaration, (form ISA/220), International Application No. PCT/GB2016/052575, dated Nov. 9, 2016 (13 pages).
Notification of the Transmittal of the International Search Report and the Written Opinion of the International Searching Authority, or the Declaration, (form ISA/220), International Application No. PCT/GB2016/052577, dated Nov. 9, 2016 (10 pages).
Notification of the Transmittal of the International Search Report and the Written Opinion of the International Searching Authority, or the Declaration, (form ISA/220), International Application No. PCT/GB2016/052578, dated Oct. 25, 2016 (12 pages).
Notification of the Transmittal of the International Search Report and the Written Opinion of the International Searching Authority, or the Declaration, (form ISA/220), International Application No. PCT/GB2016/052581, dated Oct. 24, 2016 (13 pages).
Schröder E et al., 'Arzneimittel Chemie Passage,' Arzneimittelchemie Grundlagen Nerven, Muskeln und Gewebe [Pharmaceutical Chemistry I: Basic, Nerves, Muscles and Tissues], (1ST Ed, 1976), Thieme Georg Verla, Stuttgart DE (Publ) pp. 30-33 and Table 8 XP002186820.
Tao J et al., (2013), 'Combined Treatment of BTK and PI3K Inhibitors Synergistically Disrupts BCR-Signaling, Overcomes Microenvironment-Mediated Survival and Drug Resistance in Mantle Cell Lymphoma,' Proceedings of the 104TH Annual Meeting of the American Association for Cancer Research, Apr. 6-10, 2013, Washington, D.C. Philadelphia PA, AACR Abstract #4944, Oasis, Chicago, IL (Publ) (2 pages) [retrieved on Jul. 16, 2014 at <http://wwwabstractsonline.com/Plan/ViewAbstract.aspx?Key=605> . . . ] (Abstract).
Verheijen et al., "Phosphatidylinositol 3-kinase (PI3K) inhibitors as anticancer drugs", Drugs of the Future, 2007, vol. 32, No. 6, pp. 537-547.
Yamada T et al., (2013) 'A Novel HDAC Inhibitor OBP-801 and a PI3K Inhibitor LY294002 Synergistically Induce Apoptosis via the Suppression of Survivin and XIAP in Renal Cell Carcinoma,' Int J Oncol, 43(4):1080-6.
Zhong H et al., (2013) 'Synergistic Effects of Concurrent Blockade of PI3K and MEK Pathways in Pancreatic Cancer Preclinical Models,' PLoS One, 8(10):e77243.
Zhou W et al., (2009) Novel Mutant-Selective EGFR Kinase Inhibitors Against EGFR T790M, Nature, 462(7276):1070-4 [NIH Public Access Version].

(56) References Cited

OTHER PUBLICATIONS

Cohen et al., Current Opinion in Chemical Biology, 3, 459-465, 1999.
International Preliminary Report on Patentability and Written Opinion of the International Searching Authority for PCT/GB2015/050396 dated Aug. 16, 2016 (6 pages).
International Search Report of the International Searching Authority for PCT/GB2015/050396 dated Mar. 25, 2015 (3 pages).
Somei et al., "Boronation-Thallation, A New Approach to the Synthesis of Indoles Having Aryl and/or a Heteroaryl Substituent at the 4-Position." Chem. Pharm. Bull. 1986, 34, 3971-3.
Annex to Form PCT/ISA/206 Communication relating to the results of the partial international search for International Application No. PCT/GB2016/052571 dated Nov. 9, 2016 (4 pages).
Saifuddin, M. et al., "Water-Accelerated Cationic pi-(7-endo) cyclisation: Application to Indole-Based Peri-Annulated Polyheterocycles." European Journal of Organic Chemistry, 2010, 26, 5108-5117.
Written Opinion of the International Searching Authority for PCT/GB2016/052571 dated Feb. 23, 2017 (9 pages).
International Search Report of the International Searching Authority for PCT/GB2016/052571 dated Feb. 23, 2017 (6 pages).
U.S. Appl. No. 13/384,310, Benzo [E] [1,3] Oxazin-4-One Derivatives as Phosphoinositide 3-Kinase Inhibitors, filed Feb. 6, 2012, Patented, U.S. Pat. No. 8,981,087.
U.S. Appl. No. 13/388,164, Tricyclic Heterocyclic Compounds as Phosphoinositide 3-Kinase Inhibitors, filed Mar. 27, 2012, Patented, U.S. Pat. No. 9,200,007.
U.S. Appl. No. 14/920,410, Tricyclic Heterocyclic Compounds as Phosphoinositide 3-Kinase Inhibitors, filed Oct. 22, 2015, Patented, U.S. Pat. No. 9,580,442.
U.S. Appl. No. 15/410,114, Tricyclic Heterocyclic Compounds as Phosphoinositide 3-Kinase Inhibitors, filed Jan. 19, 2017, Patented, U.S. Pat. No. 9,938,290.
U.S. Appl. No. 15/909,011, Tricyclic Heterocyclic Compounds as Phosphoinositide 3-Kinase Inhibitors, filed Mar. 1, 2018, Pending.
U.S. Appl. No. 13/643,210, Naphthridine Derivatives as PI3K Inhibitors for the Treatment of Cancer and Immune-Inflammatory, filed Jan. 7, 2013, Patented, U.S. Pat. No. 9,266,879.
U.S. Appl. No. 14/382,196, Phosphoinositide 3-Kinase Inhibitors, filed Aug. 29, 2014, Patented, U.S. Pat. No. 9,663,487.
U.S. Appl. No. 15/496,511, Phosphoinositide 3-Kinase Inhibitors, filed Apr. 25, 2017, Patented, U.S. Pat. No. 10,035,785.
U.S. Appl. No. 15/117,606, Tricyclic heterocyclic compounds as phosphoinositide 3-kinase inhibitors, filed Aug. 9, 2016, Patented, U.S. Pat. No. 9,981,987.
U.S. Appl. No. 15/961,404, Tricyclic heterocyclic compounds as phosphoinositide 3-kinase inhibitors, filed Apr. 24, 2018, Pending.
U.S. Appl. No. 15/753,361, Tricyclic heterocyclic compounds as phosphoinositide 3-kinase inhibitors, filed Feb. 19, 2018, Pending, US 2018-0244686 A1.
U.S. Appl. No. 15/753,359, Compositions comprising tricyclic heterocyclic compounds, filed Feb. 19, 2018, Pending, US 2018-0235974 A1.
U.S. Appl. No. 15/753,356, Compositions comprising a PI3K inhibitor and an HDAC inhibitor, filed Feb. 19, 2018, Pending, US 2018-0243317 A1.
U.S. Appl. No. 15/753,358, Tricyclic heterocyclic compounds as phosphoinositide 3-kinase inhibitors, filed Feb. 19, 2018, Pending, US 2018-0244685 A1.

* cited by examiner

COMPOSITIONS COMPRISING PHOSPHOINOSITIDE 3-KINASE INHIBITORS AND A SECOND ANTIPROLIFERATIVE AGENT

CROSS-REFERENCE TO RELATED APPLICATIONS

This application is the national stage application of International Patent Application No. PCT/GB2016/052575, filed Aug. 19, 2016, which claims the benefit of and priority to Great Britain Patent Application No. 1514760.6, filed Aug. 19, 2015, the contents of each of which are hereby incorporated by reference in their entirety.

FIELD OF THE INVENTION

The present invention relates to novel combinations comprising a compound which acts as an inhibitor of the class IA phosphoinositide 3-kinase enzymes, PI3K-p110δ and PI3K-p110β, in combinations with other specific anti-tumour compounds. Such combinations are useful in the therapy of cancer.

BACKGROUND OF THE INVENTION

The phosphoinositide 3-kinases (PI3Ks) constitute a family of lipid kinases involved in the regulation of a network of signal transduction pathways that control a range of cellular processes. PI3Ks are classified into three distinct subfamilies, named class I, II, and III based upon their substrate specificities. Class IA PI3Ks possess a p110α, p110β, or p110δ catalytic subunit complexed with one of three regulatory subunits, p85α, p85β or p55δ. Class IA PI3Ks are activated by receptor tyrosine kinases, antigen receptors, G-protein coupled receptors (GPCRs), and cytokine receptors. The class IA PI3Ks primarily generate phosphatidylinositol-3,4,5-triphosphate (PI(3,4,5)P$_3$), a second messenger that activates the downstream target AKT. The consequences of biological activation of AKT include tumour cell progression, proliferation, survival and growth, and there is significant evidence suggesting that the PI3K/AKT pathway is dysregulated in many human cancers. Additionally, PI3K activity has been implicated in endocrinology, cardiovascular disease, immune disorders and inflammation. It has been established that PI3K-p110δ plays a critical role in the recruitment and activation of immune and inflammatory cells. PI3K-p110δ is also upregulated in a number of human tumours and plays a key role in tumour cell proliferation and survival.

Compounds which are able to modulate p110β and p110δ activity have important therapeutic potential in cancer and immune and inflammatory disorders.

SUMMARY OF THE INVENTION

The present invention relates in part to combinations of certain PI3K compounds and certain other anti-tumour compounds. These combinations may be synergistic and therefore may offer improvements with respect to the individual components. For example, they may allow a lower dose to be administered. The present invention is based at least in part on data presented herein.

Certain PI3K inhibitors disclosed herein are also disclosed in PCT/GB2015/050396 (which is unpublished as of 19 Aug. 2015, and the contents of which are incorporated herein by reference). They may have increased activity and/or bioavailability over the compounds described in WO 2011/021038, which is also incorporated herein by reference.

The present invention is directed in part to a combination of certain PI3K inhibitors with certain anti-tumour agents.

Therefore, the present invention is a pharmaceutical composition comprising a PI3K inhibitor of Formula I:

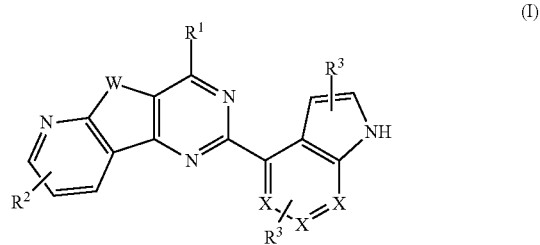

or a pharmaceutically acceptable salt thereof, wherein:

W is O, N—H, N—(C$_1$-C$_{10}$ alkyl) or S;

each X is selected independently for each occurrence from CH, CR$^3$, or

R$^1$ is a 5 to 7-membered saturated or unsaturated, optionally substituted heterocycle containing at least 1 heteroatom selected from N or O;

R$^2$ is L-Y;

each L is selected from the group consisting of a direct bond, C$_1$-C$_{10}$ alkylene, C$_2$-C$_{10}$ alkenylene and C$_2$-C$_{10}$ alkynylene;

Y is an optionally substituted fused, bridged or spirocyclic non-aromatic heterocycle containing up to 4 heteroatoms (for example, one, two, three or four heteroatoms) each independently selected from N or O, and comprising 5 to 12 carbon or heteroatoms in total; and each R$^3$ is independently H, C$_1$-C$_{10}$ alkyl, halogen, fluoro C$_1$-C$_{10}$ alkyl, O—C$_1$-C$_{10}$ alkyl, —NH—C$_1$-C$_{10}$ alkyl, S—C$_1$-C$_{10}$ alkyl, O-fluoro C$_1$-C$_{10}$ alkyl, NH-acyl, NH—C(O)—NH—C$_1$-C$_{10}$ alkyl, C(O)—NH—C$_1$-C$_{10}$ alkyl, aryl or heteroaryl;

in combination with at least one agent selected from the group consisting of signal transduction pathway inhibitors, tumour immunotherapeutics, agents inhibiting the BCL2 family of proteins, agents inhibiting Mcl-1, proteasome Inhibitors, poly (ADP-ribose) polymerase (PARP) Inhibitors, aromatase inhibitors, conventional cytotoxic agents or a miscellaneous agent selected from abiraterone, ARN-509 and MYC inhibitors.

DESCRIPTION OF THE PREFERRED EMBODIMENTS

Definitions

As used herein, "alkyl" means a C$_1$-C$_{10}$ alkyl group, which can be linear or branched. Preferably, it is a C$_1$-C$_6$ alkyl moiety. More preferably, it is a C$_1$-C$_4$ alkyl moiety. Examples include methyl, ethyl, n-propyl and t-butyl. It may be divalent, e.g. propylene.

As used herein, "alkenyl" means a C$_2$-C$_{10}$ alkenyl group. Preferably, it is a C$_2$-C$_6$ alkenyl group. More preferably, it is a C$_2$-C$_4$ alkenyl group. The alkenyl radicals may be mono- or di-saturated, more preferably monosaturated. Examples include vinyl, allyl, 1-propenyl, isopropenyl and 1-butenyl. It may be divalent, e.g. propenylene.

As used herein, "alkynyl" is a $C_2$-$C_{10}$ alkynyl group which can be linear or branched. Preferably, it is a $C_2$-$C_4$ alkynyl group or moiety. It may be divalent.

Each of the $C_1$-$C_{10}$ alkyl, $C_2$-$C_{10}$ alkenyl and $C_2$-$C_{10}$ alkynyl groups may be optionally substituted with each other, i.e. $C_1$-$C_{10}$ alkyl optionally substituted with $C_2$-$C_{10}$ alkenyl. They may also be optionally substituted with aryl, cycloalkyl (preferably $C_3$-$C_{10}$), aryl or heteroaryl. They may also be substituted with halogen (e.g. F, Cl), $NH_2$, $NO_2$ or hydroxyl. Preferably, they may be substituted with up to 10 halogen atoms or more preferably up to 5 halogens. For example, they may be substituted by 1, 2, 3, 4 or 5 halogen atoms. Preferably, the halogen is fluorine. For example, they may be substituted with $CF_3$, $CHF_2$, $CH_2CF_3$, $CH_2CHF_2$ or $CF_2CF_3$.

As used herein, the term "fluoro $C_1$-$C_{10}$ alkyl" means a $C_1$-$C_{10}$ alkyl substituted with one or more fluorine atoms. Preferably, one, two, three, four or five fluorine atoms. Examples of "fluoro $C_1$-$C_{10}$ alkyl" are $CF_3$, $CHF_2$, $CH_2F$, $CH_2CF_3$, $CH_2CHF_2$ or $CF_2CF_3$.

As used herein, "aryl" means a monocyclic, bicyclic, or tricyclic monovalent or divalent (as appropriate) aromatic radical, such as phenyl, biphenyl, naphthyl, anthracenyl, which can be optionally substituted with up to five substituents preferably selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, "heteroaryl" means a monocyclic, bicyclic or tricyclic monovalent or divalent (as appropriate) aromatic radical containing up to four heteroatoms selected from oxygen, nitrogen and sulfur, such as thiazolyl, isothiazolyl, tetrazolyl, imidazolyl, oxazolyl, isoxazolyl, thienyl, pyrazolyl, pyridinyl, pyrazinyl, pyrimidinyl, indolyl, quinolyl, isoquinolyl, triazolyl, thiadiazolyl, oxadiazolyl, said radical being optionally substituted with up to three substituents preferably selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, the term "heterocycle" or "heterocycloalkyl" is a mono- or di-valent carbocyclic radical containing up to 4 heteroatoms selected from oxygen, nitrogen and sulfur. Preferably, it contains one or two heteroatoms. Preferably, at least one of the heteroatoms is nitrogen. It may be monocyclic or bicyclic. It is preferably saturated. Examples of heterocycles are piperidine, piperazine, thiomorpholine, morpholine, azetidine or oxetane. More preferably, the heterocycle is morpholine.

The heterocyclic ring may be mono- or di-unsaturated. The radical may be optionally substituted with up to three substituents independently selected from $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, halo (e.g. F), nitro, cyano, carboxy, $C_1$-$C_3$-haloalkyl (e.g. $CF_3$), $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

In summary, each of the groups defined above, i.e., alkyl, alkenyl, alkynyl, aryl, heteroaryl, heterocycle, heterocycloalkyl, may be optionally substituted with up to three substituents preferably selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, acyl, halo (e.g. fluoro), nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

It should be noted that —NH—$C_1$-$C_{10}$ alkyl, NH-acyl, NH—C(O)—NH—$C_1$-$C_{10}$ alkyl and C(O)—NH—$C_1$-$C_{10}$ alkyl can also be written as —N—$C_1$-$C_{10}$ alkyl, N-acyl, N—C(O)—N—$C_1$-$C_{10}$ alkyl and C(O)—N—$C_1$-$C_{10}$ alkyl.

As used herein, the above groups can be followed by the suffix -ene. This means that the group is divalent, i.e. a linker group.

As used herein, the term "fused" is intended to take its usual meaning within the art of organic chemistry. Fused systems, for example fused bicyclic systems, are those in which two rings share two and only two atoms.

As used herein, the term "bridged" is intended to take its usual meaning within the art of organic chemistry. Bridged compounds are compounds which contain interlocking rings. According to the invention, the atoms of the bridged non-aromatic group which form the bridgehead is either a tertiary carbon atom (when the remaining atom is hydrogen) or a quaternary carbon atom (when the remaining atom is not hydrogen). The bridge can be considered to be a chain of atoms (for example, alkyl) or a single atom (for example, O, S, N, C) connecting two bridgeheads.

As used herein, the term "spirocyclic" is intended to take its usual meaning within the art of organic chemistry. For example, a spirocyclic compound is a bicycle whose rings are attached though just one atom (known as a spiroatom). The rings may be different in size, or they may be the same size. Preferably, according to the invention, the two rings which are joined via the same atom are non-aromatic heterocycles, preferably heterocycloalkyls. For example, the spirocyclic non-aromatic group of Formula I may be a bicycle wherein both rings are heterocycloalkyl and are attached through the same atom, preferably a carbon atom.

Compounds with which the invention is concerned which may exist in one or more stereoisomeric form, because of the presence of asymmetric atoms or rotational restrictions, can exist as a number of stereoisomers with R or S stereochemistry at each chiral centre or as atropisomeres with R or S stereochemistry at each chiral axis. The invention includes all such enantiomers and diastereoisomers and mixtures thereof.

Preferred Groups of the Invention—Compounds of Formula (I)

Preferably, a compound of the invention is as defined in claim 1, but may additionally be a compound where at least one $R^3$ is $NH_2$.

Preferably, $R^1$ is represented by any of the following structures:

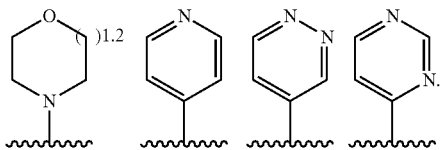

Most preferably, $R^1$ is morpholine.

In a preferred embodiment of the invention, W is oxygen or sulphur, preferably oxygen.

Preferably X is CH.

Preferably $R^3$ is H, $C_1$-$C_{10}$ alkyl, halogen or fluoro $C_1$-$C_{10}$ alkyl. More preferably $R^3$ is H.

Preferably, the 6,5-ring system in Formula I is an indole. In other words, $R^3$ is hydrogen and X is CH.

$R^2$ may be attached to any suitable atom on the aryl group, as depicted in general formula I. However, it is preferred that $R^2$ is attached to the meta-position of the pyridine ring. For example, if the nitrogen atom of the pyridine is labelled as atom number 1, then $R^2$ is attached in the 3-position.

$R^2$ is LY. Preferably, L is $C_1$-$C_{10}$ alkylene, preferably methylene.

Preferably, Y is a an optionally substituted bridged or spirocyclic heterocycloalkyl group containing up to 4 heteroatoms selected from N or O, and comprising 5 to 12 atoms in total.

Preferably, Y contains one or two heteroatoms, preferably two heteroatoms. More preferably, at least one of the heteroatoms is nitrogen and Y is bonded to L through the nitrogen atom, as depicted in the preferable Y groups below:

Formula A

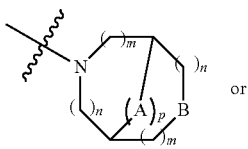

or

Formula B

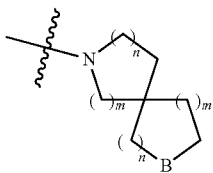

wherein:

A is selected from the group consisting of O, S, $NR^4$, optionally substituted $C_1$-$C_3$ alkylene, $C_2$-$C_3$ alkenylene and $C_2$-$C_3$ alkynylene;

B is selected from the group consisting of $NR^4$, O and $CH_2$;

wherein $R^4$ is selected from the group consisting of H, optionally substituted $C_1$-$C_{10}$ alkyl, $C_2$-$C_{10}$ alkenyl, $C_2$-$C_{10}$ alkynyl and $C_1$-$C_3$ halofluoroalkyl;

p is selected from 0, 1 or 2;

each m is independently selected from 0, 1 or 2; and each n is independently selected from 1, 2 or 3.

Preferably, A is O or $C_1$-$C_3$ alkylene, most preferably methylene.

Preferably, B is O or $CH_2$, most preferably O.

When $R^4$ is present, it is preferably H, $C_1$-$C_3$ alkyl or $C_1$-$C_3$ halofluoroalkyl. More preferably, $R^4$ is H.

Preferably, each m and n is selected so as to form 5-, 6- or 7-membered nitrogen containing heterocycloalkyl groups. Preferably, p is 1. In particular, when A is O, S or $NR^4$, p is 1.

Y is preferably bicyclic, more preferably bridged bicyclic or spirocyclic bicyclic.

Even more preferably, Y is selected from one of the following groups:

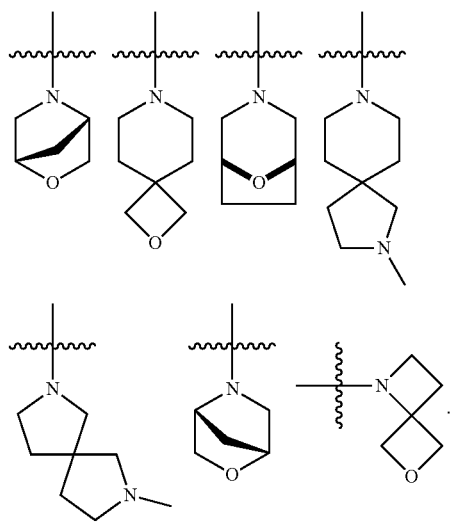

In certain embodiments, provided herein are compounds represented by:

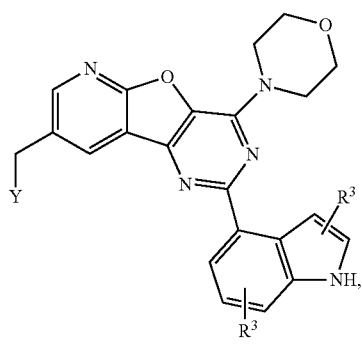

where Y and $R^3$ are defined above.

In another embodiment, provided herein are compounds represented by:

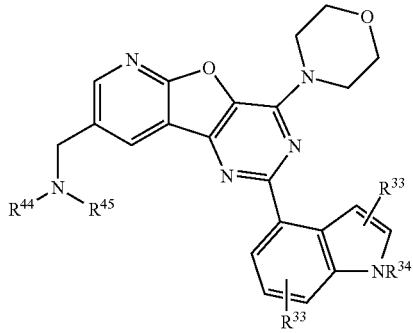

and pharmaceutically acceptable salts thereof, wherein:
R₃₃ is independently selected for each occurrence from the group consisting of H, halogen, NH—C₁₋₃alkyl, NH₂, C₁₋₆alkyl and —O—C₁₋₆alkyl (wherein C₁₋₆alkyl for each occurrence is optionally substituted by one, two or three substituents selected from halogen and hydroxyl);
R³⁴ is selected from H or C₁₋₃alkyl;
R⁴⁴ and R⁴⁵, when taken together with the nitrogen to which they are attached form a 7-10 membered bicyclic spirocycle or bridged heterocycle each having an additional heteroatom selected from O, S, or NR⁵⁵, wherein R⁵⁵ is H or C₁₋₃alkyl.

For example, R⁴⁴ and R⁴⁵, when taken together with the nitrogen to which they are attached may form a 7-8 membered bicyclic bridged heterocycle represented by:

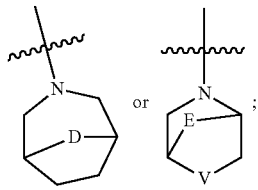

wherein D is O, S or NR⁵⁵, E is O or (CH₂)ᵣ, wherein r is 1 or 2, and V is O or NR⁵⁵, wherein R⁵⁵ is H or C₁₋₃alkyl.

In another exemplary embodiment, R⁴⁴ and R⁴⁵, when taken together with the nitrogen to which they are attached form a 7-10 membered spirocycle having one additional heteroatom selected from O or NR⁵⁵, wherein R⁵⁵ is H or C₁₋₃alkyl. Alternatively, R⁴⁴ and R⁴⁵, taken together with the nitrogen to which they are attached may be a Y substituent as described above.

Examples of structures embodying the invention are:

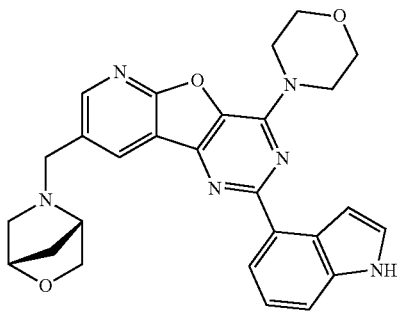

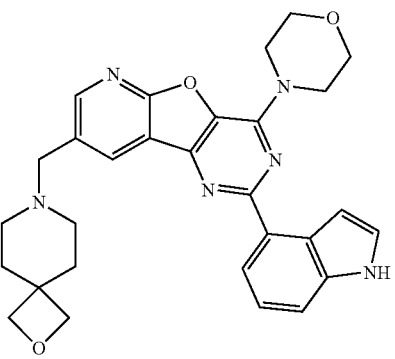

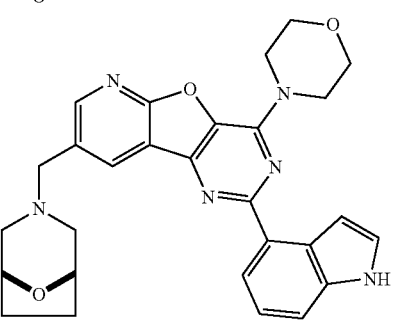

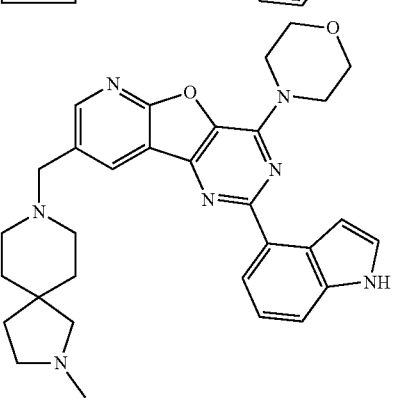

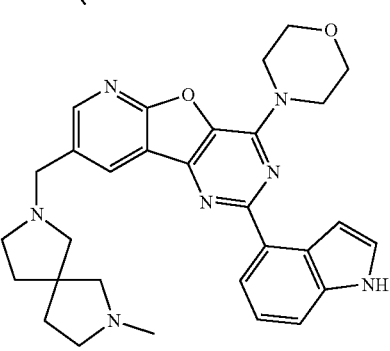

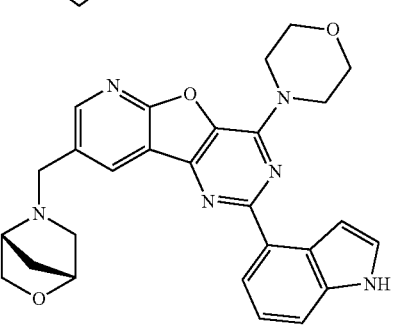

-continued

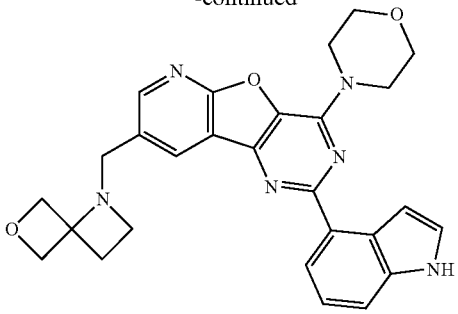

Preferred Combination Agents of the Invention

A PI3K inhibitor of formula (I) may be combined with a signal transduction pathway inhibitor.

In some embodiments, the signal transduction pathway inhibitor is selected from the list below:
- a. Bruton's tyrosine kinase (BTK) inhibitors (e.g. Ibrutinib, CC-292, CNX-774, CGI1746, LFM-A13, RN486);
- b. Spleen tyrosine kinase (SYK) inhibitors (e.g. R788 (Fostamatinib), R406, GS-9973, Piceatannol, PRT062607);
- c. BMX non-receptor tyrosine kinase inhibitors; BMX is a member of the Tec family of kinases. Inhibitors include BMX-IN-1;
- d. Anaplastic lymphoma kinase (ALK) inhibitors (e.g. Ceritinib, Crizotinib, TAE684, AP26113, Alectinib, PF-06463922, GSK1838705A, AZD3463, ASP3016;
- e. Small molecule inhibitors of—and biological agents targeting—tyrosine kinases including growth factor receptor tyrosine kinases, such as:
  - i. the epidermal growth factor receptor (EGFR) (e.g. Trastuzumab, Cetixumab, Panitumumab, Zalutumumab, Nimotuzumab, Matuzumab, Gefitinib, Erlotinib, Lapatinib, AP26113);
  - ii. the platelet-derived growth factor receptor (PDGFR) (e.g. Sorafenib, Sunitinib, Cabozantinib, Axitinib, AZD2932, Dovitinib, LY2874455, Foretinib, Vandetanib, SKLB1002, BMS-794833, Ki8751, Apatinib, AEE788, Tivozanib, Brivanib, ENMD-2076, Lenvatinib, OSI-930, Pazopanib, RAF265, CYC116, PD173074, PD173074, KRN633, Cabozantinib, ZM306416, Golvatinib, ZM323881, Semaxanib, SAR131675, MGCD-265, Orantinib, Vantanalib, Cediranib, Regorafenib);
  - iii. the fibroblast growth factor receptor (FGFR) (e.g. Ponatinib, BGJ398, Nintedanib, PD173074, CH5183284, LY2874455, AZD4547, Danusertib, Tyrphostin, SSR128129E, MK-2461, Brivanib, TSU-68);
  - iv. the vascular endothelial growth factor receptor (VEGFR) (e.g. Cabozantinib, PD153035).
- f. Vascular endothelial growth factor (VEGF) inhibitors (e.g. Bevacizumab, Ranibizumab).
- g. Small molecule inhibitors of the ribosomal protein S6 kinase, p-70S6K (e.g. LY2584702, BI-D1870, PF-4708671, AT7867, AT13148).
- h. Inhibitors of mammalian target of rapamycin (mTOR) (e.g. Sirolimus, Everolimus, AZD8055, Temsirolimus, MHY1485, Zotarolimus, KU-0063794, ETO-46464, GDC-0349, XL388, WYE-354, WYE-125132, WAY-600, WYE-687, PP121, AZD2014, INK128, Voxtalisib, Ridaforolimus, Torkinib, OSI-027, Palomid 529).
- i. RAF kinase inhibitors (e.g. Vemurafenib, Dabrafenib, Sorafenib, PLX-4720, LY3009120, RAF265, AZ638, Encorafenib, GDC-0879, CEP-32496, TAK-632, ZM-336372, NVP-BHG712, SB590885, GW5074);
- j. Mitogen-activated protein kinase (MEK) inhibitors (e.g. Trametinib, Selumetinib, PD0325901, U0126, PD184352, GDC-0623, BI-847325, Cobimetinib, PD98059, BIX-02189, Binimetinib, Pimasertib, CL-327, AZD8330, TAK-733, PD318088, Redametinib);
- k. BCR-ABL inhibitors (e.g. Imatinib, Dasatinib, Saracatinib, Nilotinib, Ponatinib, PD173955, Danusertib, AT9283, GNF-5, GZD824, KW-2449, DCC-2036, NVP-BHG712, GNF-2, Baferinib, Degrasyn);
- l. Extracellular signal-regulated kinase (ERK) inhibitors (e.g. SCH772984, XMD8-92, FR-180204, GDC-0994, ERK5-IN-1, Ulixertinib);
- m. JAK-STAT signalling inhibitors (e.g. Pacritinib, Tofacitinib, AZD1480, Ruxolitinib, Fedratinib, AT9283, Cerdulatinib, Filgotinic, Go6976, AG-490, Momelotinib, GLPG0634, ZM039923, ZL019, Curcumol, CEP-33779, AZ-960, TG1011209, NVP-BSK805, Baricitinib, AP1066, WHI-P154, Gandotinib);
- n. NF-κB-inducing kinase (NIK) inhibitors.

A compound of formula (I) may be combined with a tumor immunotherapeutic.

In some embodiments, the tumour immunotherapeutic is selected from the list below:

Small Molecules
- a. HDAC6 inhibitors;
- b. Indoleamine-2,3-dioxygenase (IDO) inhibitors (e.g. NLG919, INCB024360, Indoximod);
- c. Immunomodulators (IMiDs) (e.g. Lenalidomide, Pomalidomide, Thalidomide);

Biological Agents
- a. Anti-PD-1 agents: (e.g. Pembrolizumab, Nivolumab, Pidilizumab, AMP-224);
- b. Anti-PD-L1 agents (e.g. MSB0010718C, Atezolizumab, MED14736, MPDL3280A),
- c. CTLA-4-targeted agents (e.g. Ipilimumab).

A compound of formula (I) may be combined with Agents inhibiting the BCL2 family of proteins (such as BCL-2, BCL-xL, BCL-w). Examples include ABT-737, ABT-263, Obatoclax, Venetoclax, Sabutoclax, AT101, HA14-1, BAM7.

A compound of formula (I) may be combined with an agent inhibiting Mcl-1 (e.g. UMI-77).

A compound of formula (I) may be combined with Proteasome Inhibitors (e.g. Carfilzomib, /Bortezomib, MG-132, MLN9708, Ixazomib, ONX-0914, Oprozomib, PI-1840, CEP-18770, Celastrol).

A compound of formula (I) may be combined with Poly (ADP-ribose) polymerase (PARP) Inhibitors (e.g. Olaparib, Veliparib, Rucaparib, Iniparib, Talazoparib, G007-LK, NU1025, AG-14361, INO-1001, UPF-1069, AZD-2461, PJ34, ME0328, A-966492).

A compound of formula (I) may be combined with Aromatase inhibitors (e.g. Letrozole, Anastrazole).

A compound of formula (I) may be combined with Conventional cytotoxic agents including: platinum complexes, e.g. cisplatin and carboplatin; mitoxantrone; vinca alkaloids e.g. vincristine and vinblastine; anthracycline antibiotics, e.g. daunorubicin and doxorubicin; alkylating agents, e.g. chlorambucil and melphalan; taxanes e.g. paclitaxel; antifolates, e.g. methotrexate and tomudex; epipodophyllotoxins, e.g. etoposide; camptothecins, e.g. irinotecan and its active metabolite SN38; DNA methylation inhibitors, e.g. the DNA methylation inhibitors disclosed in WO02/085400.

A compound of formula (I) may be combined with a miscellaneous agent selected from Abiraterone, ARN-509, MYC inhibitors.

General Description—Compositions (Combinations)

A pharmaceutical composition of the invention comprises a compound/combination as defined above, and a pharmaceutically acceptable carrier or diluent. A pharmaceutical composition of the invention typically contains up to 85 wt % of a compound of the invention. More typically, it contains up to 50 wt % of a compound of the invention. Preferred pharmaceutical compositions are sterile and pyrogen-free. Further, the pharmaceutical compositions provided by the invention typically contain a compound of the invention which is a substantially pure optical isomer. Preferably, the pharmaceutical composition comprises a pharmaceutically acceptable salt form of a compound of the invention. For example, contemplated herein is a pharmaceutically acceptable composition comprising a disclosed compound and a pharmaceutically acceptable excipient.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulfonic, ethanesulfonic, salicylic, stearic, benzenesulfonic or p-toluenesulfonic acid. Pharmaceutically acceptable bases include alkali metal (e.g. sodium or potassium) and alkali earth metal (e.g. calcium or magnesium) hydroxides and organic bases such as alkyl amines, aryl amines or heterocyclic amines.

For the avoidance of doubt, the present invention also embraces prodrugs which react in vivo to give a compound of the present invention.

The compounds of the invention may be prepared by synthetic routes that will be apparent to those skilled in the art, e.g. based on the Examples.

The compounds of the invention and compositions comprising them may be administered in a variety of dosage forms. In one embodiment, a pharmaceutical composition comprising a compound of the invention may be formulated in a format suitable for oral, rectal, parenteral, intranasal or transdermal administration or administration by inhalation or by suppository. Typical routes of administration are parenteral, intranasal or transdermal administration or administration by inhalation.

The compounds of the invention can be administered orally, for example as tablets, troches, lozenges, aqueous or oily suspensions, dispersible powders or granules. Preferred pharmaceutical compositions of the invention are compositions suitable for oral administration, for example tablets and capsules. In some embodiments, disclosed compounds may have significantly higher oral bioavailability as compared to compounds having a non-spirocycle or non-bridged heterocyclic moiety, e.g., at $R^2$ above.

The compounds of the invention may also be administered parenterally, whether subcutaneously, intravenously, intramuscularly, intrasternally, transdermally or by infusion techniques. The compounds may also be administered as suppositories.

The compounds of the invention may also be administered by inhalation. An advantage of inhaled medications is their direct delivery to the area of rich blood supply in comparison to many medications taken by oral route. Thus, the absorption is very rapid as the alveoli have an enormous surface area and rich blood supply and first pass metabolism is bypassed. A further advantage may be to treat diseases of the pulmonary system, such that delivering drugs by inhalation delivers them to the proximity of the cells which are required to be treated.

The present invention also provides an inhalation device containing such a pharmaceutical composition. Typically said device is a metered dose inhaler (MDI), which contains a pharmaceutically acceptable chemical propellant to push the medication out of the inhaler.

The compounds of the invention may also be administered by intranasal administration. The nasal cavity's highly permeable tissue is very receptive to medication and absorbs it quickly and efficiently, more so than drugs in tablet form. Nasal drug delivery is less painful and invasive than injections, generating less anxiety among patients. By this method absorption is very rapid and first pass metabolism is usually bypassed, thus reducing inter-patient variability. Further, the present invention also provides an intranasal device containing such a pharmaceutical composition.

The compounds of the invention may also be administered by transdermal administration. The present invention therefore also provides a transdermal patch containing a compound of the invention.

The compounds of the invention may also be administered by sublingual administration. The present invention therefore also provides a sub-lingual tablet comprising a compound of the invention.

A compound of the invention may also be formulated with an agent which reduces degradation of the substance by processes other than the normal metabolism of the patient, such as anti-bacterial agents, or inhibitors of protease enzymes which might be the present in the patient or in commensural or parasite organisms living on or within the patient, and which are capable of degrading the compound.

Liquid dispersions for oral administration may be syrups, emulsions and suspensions.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

Where a kit and/or a method of the invention provides for the administration of more than one drug, they can be administered simultaneous, sequentially or separately. It is not necessary that they are packed together (but this is one embodiment of the invention). It is also not necessary that they are administered at the same time or that they are in the same dosage form. As used herein, "separate" administration means that the drugs are administered as part of the same overall dosage regimen (which could comprise a number of days), but preferably on the same day. As used herein "simultaneously" means that the drugs are to be taken together or formulated as a single composition. As used herein, "sequentially" means that the drugs are administered at about the same time, and preferably within about 1 hour of each other.

In some embodiments, a disclosed PI3K inhibitor may be administered at certain dosages (e.g., lower dosages than monotherapy) but may be therapeutically effective when combined with certain anti-tumour compounds such as those disclosed herein). For example, the combination of the PI3K inhibitor of Formula I and certain anti-tumour compounds disclosed herein may achieve a synergistic effect in the treatment of the subject in need thereof, wherein the combination is administered at dosages that would not be effective when one or both of the compounds are administered alone, but which amounts are effective in combination.

General Disclosure—Methods of Use

The compositions of the present invention can be used in both the treatment and prevention of cancer and can be used in a combination therapy of the invention or in further combination. When used in a further combination therapy, the compounds of the present invention are typically used together with small chemical compounds such as platinum complexes, anti-metabolites, DNA topoisomerase inhibitors, radiation, antibody-based therapies (for example herceptin and rituximab), anti-cancer vaccination, gene therapy, cellular therapies, hormone therapies or cytokine therapy.

In one embodiment of the invention a composition of the invention is used in further combination with another chemotherapeutic or antineoplastic agent in the treatment of a cancer. Examples of such other chemotherapeutic or antineoplastic agents include platinum complexes including cisplatin and carboplatin, mitoxantrone, vinca alkaloids for example vincristine and vinblastine, anthracycline antibiotics for example daunorubicin and doxorubicin, alkylating agents for example chlorambucil and melphalan, taxanes for example paclitaxel, antifolates for example methotrexate and tomudex, epipodophyllotoxins for example etoposide, camptothecins for example irinotecan and its active metabolite SN38 and DNA methylation inhibitors for example the DNA methylation inhibitors disclosed in WO02/085400.

According to the invention, therefore, products are provided which contain a composition of the invention and another chemotherapeutic or antineoplastic agent as a combined preparation for simultaneous, separate or sequential use in alleviating a cancer. Also provided according to the invention is the use of compound of the invention in the manufacture of a medicament for use in the alleviation of cancer by coadministration with another chemotherapeutic or antineoplastic agent. The compound of the invention and the said other agent may be administered in any order. In both these cases the compound of the invention and the other agent may be administered together or, if separately, in any order as determined by a physician.

The combinations of the present invention may also be used to treat abnormal cell proliferation due to insults to body tissue during surgery in a human patient. These insults may arise as a result of a variety of surgical procedures such as joint surgery, bowel surgery, and cheloid scarring. Diseases that produce fibrotic tissue that may be treated using the combinations of the present invention include emphysema. Repetitive motion disorders that may be treated using the present invention include carpal tunnel syndrome. An example of a cell proliferative disorder that may be treated using the invention is a bone tumour.

Proliferative responses associated with organ transplantation that may be treated using combinations of the invention include proliferative responses contributing to potential organ rejections or associated complications. Specifically, these proliferative responses may occur during transplantation of the heart, lung, liver, kidney, and other body organs or organ systems.

Abnormal angiogenesis that may be treated using this invention include those abnormal angiogenesis accompanying rheumatoid arthritis, ischemic-reperfusion related brain edema and injury, cortical ischemia, ovarian hyperplasia and hypervascularity, polycystic ovary syndrome, endometriosis, psoriasis, diabetic retinopathy, and other ocular angiogenic diseases such as retinopathy of prematurity (retrolental fibroplastic), macular degeneration, corneal graft rejection, neuroscular glaucoma and Osler Weber-Rendu syndrome.

Examples of diseases associated with uncontrolled angiogenesis that may be treated according to the present invention include, but are not limited to retinal/choroidal neovascularisation and corneal neovascularisation. Examples of diseases which include some component of retinal/choroidal neovascularisation include, but are not limited to, Best's diseases, myopia, optic pits, Stargart's diseases, Paget's disease, vein occlusion, artery occlusion, sickle cell anaemia, sarcoid, syphilis, pseudoxanthoma elasticum carotid apo structive diseases, chronic uveitis/vitritis, mycobacterial infections, Lyme's disease, systemic lupus erythematosus, retinopathy of prematurity, Eale's disease, diabetic retinopathy, macular degeneration, Bechet's diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularisation of the angle) and diseases caused by the abnormal proliferation of fibrovascular or fibrous tissue including all forms of proliferative vitreoretinopathy. Examples of corneal neovascularisation include, but are not limited to, epidemic keratoconjunctivitis, Vitamin A deficiency, contact lens overwear, atopic keratitis, superior limbic keratitis, pterygium keratitis sicca, Sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, mycobacteria infections, lipid degeneration, chemical burns, bacterial ulcers, fungal ulcers, Herpes simplex infections, Herpes zoster infections, protozoan infections and Kaposi sarcoma.

Chronic inflammatory diseases associated with uncontrolled angiogenesis may also be treated using combinations of the present invention. Chronic inflammation depends on continuous formation of capillary sprouts to maintain an influx of inflammatory cells. The influx and presence of the inflammatory cells produce granulomas and thus maintains the chronic inflammatory state. Inhibition of angiogenesis using a PI3K inhibitor alone or in conjunction with other anti-inflammatory agents may prevent the formation of the granulosmas and thus alleviate the disease. Examples of chronic inflammatory diseases include, but are not limited to, inflammatory bowel diseases such as Crohn's disease and ulcerative colitis, psoriasis, sarcoidosis, and rheumatoid arthritis.

Inflammatory bowel diseases such as Crohn's disease and ulcerative colitis are characterised by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhoea associated with abdominal pain, fever, anorexia, weight loss and abdominal swelling. Ulcerative colitis is also a chronic, nonspecific, inflammatory and ulcerative disease arising in the colonic mucosa and is characterised by the presence of bloody diarrhoea. These inflammatory bowel diseases are generally caused by chronic granulomatous inflammation throughout the gastrointestinal tract, involving new capillary sprouts surrounded by a cylinder of inflammatory cells. Inhibition of angiogenesis by these inhibitors should inhibit the formation of the sprouts and prevent the formation of granulomas. Inflammatory bowel diseases also exhibit extra intestinal manifestations, such as skin lesions. Such lesions are characterized by inflammation and angiogenesis and can occur at many sites other than the gastrointestinal tract. Inhibition of angiogenesis by combinations according to the present invention can reduce the influx of inflammatory cells and prevent lesion formation.

Sarcoidosis, another chronic inflammatory disease, is characterized as a multisystem granulomatous disorder. The granulomas of this disease can form anywhere in the body. Thus, the symptoms depend on the site of the granulomas and whether the disease is active. The granulomas are created by the angiogenic capillary sprouts providing a constant supply of inflammatory cells. By using combinations according to the present invention to inhibit angiogenesis, such granulomas formation can be inhibited. Psoriasis, also a chronic and recurrent inflammatory disease, is characterised by papules and plaques of various sizes. Treatment using these inhibitors alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterised by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using combinations according to the present invention alone or in conjunction with other anti-RA agents may prevent the formation of new blood vessels necessary to maintain the chronic inflammation.

Preferably, the condition is cancer, notably leukaemias including chronic myelogenous leukaemia and acute myeloid leukaemia, lymphomas, solid tumours, and PTEN-negative and/or PTEN-defective tumours including PTEN-negative haematological, breast, lung, endometrial, skin, brain and prostate cancers (where PTEN refers to "phosphatise and tensin homolog deleted on chromosome 10"). More preferably, the condition to be treated in a patient in need thereof by administering an effective amount of a disclosed compound is a disorder selected from rheumatoid arthritis, asthma, chronic obstructive pulmonary disease (COPD), multiple sclerosis, psoriasis and other inflammatory skin disorders, systemic lupus erythematosus, inflammatory bowel disease, and organ transplant rejection. For example, provided herein is a method of treating a patient suffering a disorder selected from the group consisting leukaemias (including e.g., chronic myelogenous leukaemia and acute myeloid leukaemia), lymphoma, a solid tumour cancer such as breast, lung, or prostate cancer, PTEN-negative tumours including PTEN-negative haematological, breast, lung, endometrial, skin, brain and prostate cancers (where PTEN refers to "phosphatase and tensin homolog deleted on chromosome 10") comprising administering an effective amount of a disclosed compound.

HDAC is believed to contribute to the pathology and/or symptomology of several different diseases such that reduction of the activity of HDAC in a subject through inhibition of HDAC may be used to therapeutically address these disease states. Examples of various diseases that may be treated using the combinations of the present invention are described herein.

One set of indications that combinations of the present invention may be used to treat is those involving undesirable or uncontrolled cell proliferation. Such indications include benign tumours, various types of cancers such as primary tumours and tumour metastasis, restenosis (e.g. coronary, carotid, and cerebral lesions), abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants. More specific indications for combinations include, but are not limited to prostate cancer, lung cancer, acute leukaemia, multiple myeloma, bladder carcinoma, renal carcinoma, breast carcinoma, colorectal carcinoma, neuroblastoma and melanoma.

In one embodiment, a method is provided for treating diseases associated with undesired and uncontrolled cell proliferation. The method comprises administering to a subject suffering from uncontrolled cell proliferation a therapeutically effective amount of a HDAC inhibitor according to the present invention, such that said uncontrolled cell proliferation is reduced. The particular dosage of the inhibitor to be used will depend on the severity of the disease state, the route of administration, and related factors that can be determined by the attending physician. Generally, acceptable and effective daily doses are amounts sufficient to effectively slow or eliminate uncontrolled cell proliferation.

Combinations according to the present invention may also be used in conjunction with other agents to inhibit undesirable and uncontrolled cell proliferation. Examples of other anti-cell proliferation agents that may be used in conjunction with the combinations of the present invention include, but are not limited to, retinoid acid and derivatives thereof, 2-methoxyestradiol, Angiostatin™ protein, Endostatin™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulfate (clupeine), sulfated chitin derivatives (prepared from queen crab shells), sulfated polysaccharide peptidoglycan complex (sp-pg), staurosporine, modulators of matrix metabolism, including for example, proline analogs ((1-azetidine-2-carboxylic acid (LACA), cishydroxyproline, d,I-3,4-dehydroproline, thiaproline), beta-aminopropionitrile fumarate, 4-propyl-5-(4-pyridinyl)-2(3H)-oxazolone; methotrexate, mitoxantrone, heparin, interferons, 2 macroglobulin-serum, chimp-3, chymostatin, beta-cyclodextrin tetradecasulfate, eponemycin; fumagillin, gold sodium thiomalate, d-penicillamine (CDPT), beta-1-anticollagenase-serum, alpha-2-antiplasmin, bisantrene, lobenzarit disodium, n-(2-carboxyphenyl-4-chloroanthronilic acid disodium or "CCA", thalidomide; angiostatic steroid, carboxyaminoimidazole; metalloproteinase inhibitors such as BB94. Other anti-angiogenesis agents that may be used include antibodies, preferably monoclonal antibodies against these angiogenic growth factors: bFGF, aFGF, FGF-5, VEGF isoforms, VEGF-C, HGF/SF and Ang-1/Ang-2. Ferrara N. and Alitalo, K. "Clinical application of angiogenic growth factors and their inhibitors" (1999) Nature Medicine 5:1359-1364.

Generally, cells in benign tumours retain their differentiated features and do not divide in a completely uncontrolled manner. A benign tumour is usually localized and nonmetastatic. Specific types of benign tumours that can be treated using combinations of the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In the case of malignant tumors, cells become undifferentiated, do not respond to the body's growth control signals, and multiply in an uncontrolled manner. Malignant tumors are invasive and capable of spreading to distant sites (metastasizing). Malignant tumors are generally divided into two categories: primary and secondary. Primary tumors arise directly from the tissue in which they are found. Secondary tumours, or metastases, are tumours that originated elsewhere in the body but have now spread to distant organs. Common routes for metastasis are direct growth into adjacent structures, spread through the vascular or lymphatic systems, and tracking along tissue planes and body spaces (peritoneal fluid, cerebrospinal fluid, etc.).

Specific types of cancers or malignant tumours, either primary or secondary, that can be treated using the combinations of the present invention include, but are not limited to, leukaemia, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumour, small-cell lung tumour, gallstones, islet cell tumour, primary brain tumour, acute and chronic lymphocytic and granulocytic tumours, hairy-cell tumour, adenoma, hyperplasia, medullary carcinoma, pheochromocytoma, mucosal neuromas, intestinal ganglloneuromas, hyperplastic corneal nerve tumour, marfanoid habitus tumour, Wilms' tumour, seminoma, ovarian tumour, leiomyomater tumour, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumour, polycythermia vera, adenocarcinoma, glioblastoma multiforme, leukemias, lymphomas, malignant melanomas, epidermoid carcinomas, and other carcinomas and sarcomas.

The combinations of the present invention may also be used to treat abnormal cell proliferation due to insults to body tissue during surgery. These insults may arise as a result of a variety of surgical procedures such as joint surgery, bowel surgery, and cheloid scarring. Diseases that produce fibrotic tissue that may be treated using the combinations of the present invention include emphysema. Repetitive motion disorders that may be treated using the present invention include carpal tunnel syndrome. An example of a cell proliferative disorder that may be treated using the invention is a bone tumour.

Proliferative responses associated with organ transplantation that may be treated using combinations of the invention include proliferative responses contributing to potential organ rejections or associated complications. Specifically, these proliferative responses may occur during transplantation of the heart, lung, liver, kidney, and other body organs or organ systems.

Sarcoidosis, another chronic inflammatory disease, is characterized as a multisystem granulomatous disorder. The granulomas of this disease can form anywhere in the body. Thus, the symptoms depend on the site of the granulomas and whether the disease is active. The granulomas are created by the angiogenic capillary sprouts providing a constant supply of inflammatory cells. By using combinations according to the present invention to inhibit angiogenesis, such granulomas formation can be inhibited. Psoriasis, also a chronic and recurrent inflammatory disease, is characterized by papules and plaques of various sizes. Treatment using these inhibitors alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using combinations according to the present invention alone or in conjunction with other anti-RA agents may prevent the formation of new blood vessels necessary to maintain the chronic inflammation.

The compounds of the present invention can further be used in the treatment of cardiac/vasculature diseases such as hypertrophy, hypertension, myocardial infarction, reperfusion, ischaemic heart disease, angina, arrhythmias, hypercholesterolemia, atherosclerosis and stroke. The compounds can further be used to treat neurodegenerative disorders/CNS disorders such as acute and chronic neurological diseases, including stroke, Huntington's disease, Amyotrophic Lateral Sclerosis and Alzheimer's disease.

The compounds of the present invention can also be used as antimicrobial agents, for example antibacterial agents. The invention therefore also provides a compound for use in the treatment of a bacterial infection. The compounds of the present invention can be used as anti-infectious compounds against viral, bacterial, fungal and parasitic infections. Examples of infections include protozoal parasitic infections (including plasmodium, cryptosporidium parvum, toxoplasma gondii, sarcocystis neurona and *Eimeria* sp.)

The compounds of the present invention are particularly suitable for the treatment of undesirable or uncontrolled cell proliferation, preferably for the treatment of benign tumours/hyperplasias and malignant tumours, more preferably for the treatment of malignant tumours and most preferably for the treatment of chronic lymphocytic leukaemia (CLL), breast cancer, prostate cancer, ovarian cancer, mesothelioma, T-cell lymphoma.

In a preferred embodiment of the invention, the compounds of the invention are used to alleviate cancer, cardiac hypertrophy, chronic heart failure, an inflammatory condition, a cardiovascular disease, a haemoglobinopathy, a thalassemia, a sickle cell disease, a CNS disorder, an autoimmune disease, organ transplant rejection, diabetes, osteoporosis, MDS, benign prostatic hyperplasia, oral leukoplakia, a genetically related metabolic disorder, an infection, Rubens-Taybi, fragile X syndrome, or alpha-1 antitrypsin deficiency, or to accelerate wound healing, to protect hair follicles or as an immunosuppressant.

Typically, said inflammatory condition is a skin inflammatory condition (for example psoriasis, acne and eczema), asthma, chronic obstructive pulmonary disease (COPD), rheumatoid arthritis (RA), inflammatory bowel disease (IBD), Crohn's disease or colitis.

Typically, said cancer is chronic lymphocytic leukaemia, breast cancer, prostate cancer, ovarian cancer, mesothelioma or T-cell lymphoma.

Typically, said cardiovascular disease is hypertension, myocardial infarction (MI), ischemic heart disease (IHD) (reperfusion), angina pectoris, arrhythmia, hypercholesterolemia, hyperlipidaemia, atherosclerosis, stroke, myocarditis, congestive heart failure, primary and secondary i.e. dilated (congestive) cardiomyopathy, hypertrophic cardiomyopathy, restrictive cardiomyopathy, peripheral vascular disease, tachycardia, high blood pressure or thrombosis.

Typically, said genetically related metabolic disorder is cystic fibrosis (CF), peroxisome biogenesis disorder or adrenoleukodystrophy.

Typically, the compounds of the invention are used as an immunosuppressant following organ transplant.

Typically, said infection is a viral, bacterial, fungal or parasitic infection, in particular an infection by *S aureus, P acne, candida* or *aspergillus*.

Typically, said CNS disorder is Huntingdon's disease, Alzheimer's disease, multiple sclerosis or amyotrophic lateral sclerosis.

In this embodiment, the compounds of the invention may be used to alleviate cancer, cardiac hypertrophy, chronic heart failure, an inflammatory condition, a cardiovascular disease, a haemoglobinopathy, a thalassemia, a sickle cell disease, a CNS disorder, an autoimmune disease, diabetes or osteoporosis, or are used as an immunosuppressant.

The compounds of the invention may also be used to alleviate chronic lymphocytic leukaemia (CLL), breast cancer, prostate cancer, ovarian cancer, mesothelioma, T-cell lymphoma, cardiac hypertrophy, chronic heart failure or a skin inflammatory condition, in particular psoriasis, acne or eczema.

The compounds of the present invention can be used in the treatment of animals, preferably in the treatment of mammals and more preferably in the treatment of humans.

The compounds of the invention may, where appropriate, be used prophylactically to reduce the incidence of such conditions.

In use, a therapeutically effective amount of a compound of the invention is administered to a patient. A typical dose is from about 0.001 to 50 mg per kg of body weight, according to the activity of the specific compound, the age, weight and conditions of the subject to be treated, the type and severity of the disease and the frequency and route of administration.

The invention will now be illustrated by the following Examples.

EXAMPLES

Synthesis of Intermediate X (a Precursor to the Compounds of Formula I)

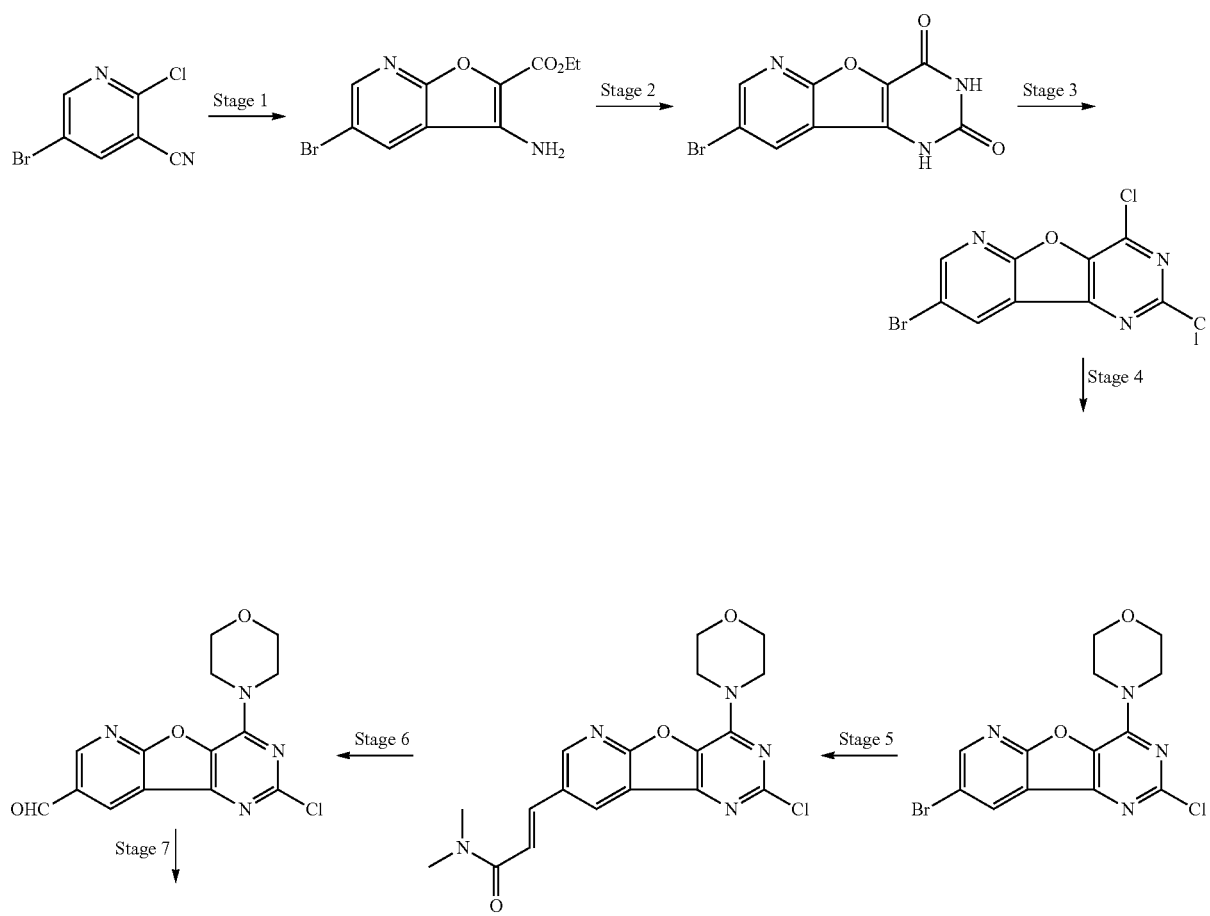

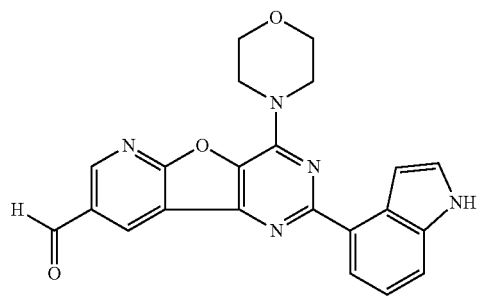

Intermediate X

Reagents and conditions: 1) K$_2$CO$_3$, ethyl glycolate, DMF, 115° C.; 2) (i) chlorosulfonyl isocyanate, CH$_2$Cl$_2$, 0-10° C. then rt (ii) water, 75° C. (iii) NaOH max temp 40° C., 3) POCl$_3$, N,N-dimethylaniline, 107° C., 4) morpholine, MeOH, rt, 5) N,N,-dimethylacrylamide, PdCl$_2$(PPh$_3$)$_2$, NaOAc, DMF, 110° C.; 6) NaIO$_4$, OsO$_4$, THF, water, rt; 7) indole-4-boronic acid pinacol ester, PdCl$_2$(PPh$_3$)$_2$, sodium carbonate, dioxane, water, 102° C.

i. Ethyl-3-amino-5-bromofuro[2,3-b]pyridine-2-carboxylate

To a 10 L flask under N$_2$ (g) was added 5-bromo-2-chloropyridine-3-carbonitrile (435 g, 2.0 mol, 1 eq), DMF (2790 mL) and potassium carbonate (553 g, 4.0 mol, 2 eq). This was followed by the addition of ethyl glycolate (208.2 mL, 2.2 mol, 1.1 eq). The reaction mixture was heated to 115° C. overnight. Upon completion, the reaction mixture was cooled to rt and water (13.1 L) was added, this led to the formation of a precipitate. The mixture was stirred for 20 mins, then filtered. The resulting brown solid was dried at 50° C., slurried in Et$_2$O:heptane (9:1, 2.8 L) and filtered to give 405.6 g. Further purification via soxhlet extraction using TBME (4.5 L) yielded the product as a yellow solid (186 g, 34%). This procedure was repeated twice.

$^1$H NMR (400 MHz, CDCl$_3$) $\delta_H$: 8.53 (d, J=2.0 Hz, 1H), 8.07 (d, J=2.0 Hz, 1H), 5.00 (br. s., 2H), 4.44 (q, J=7.0 Hz, 2H), 1.44 (t, J=7.0 Hz, 3H).

MS (ES$^+$) 309 (100%, [M+Na]$^+$), 307 (100%, [M+Na]$^+$).

ii. 12-Bromo-8-oxa-3,5,10-triazatricyclo[7.4.0.0$^{2,7}$]trideca-1(9),2(7), 10,12-tetraene-4,6-dione To ethyl-3-amino-5-bromofuro[2,3-b]pyridine-2-carboxylate (239.0 g, 0.84 mol, 1 eq) dissolved in CH$_2$Cl$_2$ (5.5 L) was added chlorosulfonyl isocyanate (87.6 mL, 1.0 mol, 1.2 eq) dropwise at 0-10° C. The resulting reaction was stirred for 30 min, stripped to dryness and the resulting solid ground to a fine powder. Water (5.5 L) was added to the solid and the suspension was heated at 75° C. for 1 h. After cooling to rt, solid NaOH (335 g, 8.4 mol, 10 eq) was added allowing the reaction to exotherm (maximum temperature 40° C.). The reaction was cooled to 0-10° C. and the pH adjusted to 5-6 using 5M HCl (~1 L). The reaction was stirred for 30 mins, then filtered. The solid was washed with water (2.3 L) and pulled dry. Further drying in a vacuum oven at 40° C. yielded the product as a brown solid (193 g, 76%). This procedure was repeated twice.

$^1$H NMR (400 MHz, DMSO-d$_6$) $\delta_H$: 12.01 (br. s., 1H), 11.58 (br. s, 1H), 8.72 (d, J=2.0 Hz, 1H), 8.59 (d, J=2.0 Hz, 1H).

MS (ES$^-$) 282 (100%, [M+H]$^+$).

iii. 12-Bromo-4,6-dichloro-8-oxa-3,5,10-triazatricyclo[7.4.0.0$^{2,7}$]trideca-1(9),2(7),3,5,10,12-hexaene To 12-bromo-8-oxa-3,5,10-triazatricyclo[7.4.0.0$^{2,7}$]trideca-1(9),2(7), 10,12-tetraene-4,6-dione (387 g, 1.27 mol, 1 eq) was added POCl$_3$ (6070 mL) and N,N-dimethylaniline (348 mL, 2.8 mol, 2.2 eq). The mixture was heated at 107° C. for 10 h. Once cooled to rt, solvent was removed in vacuo azeotroping with toluene (3×3.9 L). The resulting residue was partitioned between CH$_2$Cl$_2$ (12.76 L) and water (3.9 L) and the phases separated. The organic phase was washed with water (2×3.9 L). The combined aqueous was back-extracted with CH$_2$Cl$_2$ (7.7 L) and the combined organics dried over MgSO$_4$, filtered and stripped to yield the product as brown solid (429 g, ~quant.).

$^1$H NMR (400 MHz, CDCl$_3$) $\delta_H$: 8.78 (d, J=2.5 Hz, 1H), 8.72 (d, J=2.5 Hz, 1H).

iv. 12-bromo-4-chloro-6-(morpholin-4-yl)-8-oxa-3,5,10-triazatricyclo [7.4.0.0$^{2,7}$]trideca-1(9),2(7),3,5,10,12-hexaene To 12-bromo-4,6-dichloro-8-oxa-3,5,10-triazatricyclo [7.4.0.0$^{2,7}$]trideca-1(9),2(7),3,5,10,12-hexaene (419.3 g, 1.32 mol, 1 eq) in MeOH (8588 mL) was added Morpholine (259 mL, 2.90 mol, 2.2 eq) at rt. After stirring for 2 h, water (0.8 L) was added. It was then cooled to 0-5° C. and stirred for an additional 30 mins. The resulting solid was filtered, washed with water (5.2 L) and pulled dry. Further purification by silica gel column chromatography with CH$_2$Cl$_2$/EtOAc (1:0-9:1) yielded the desired product (419 g, 84%).

$^1$H NMR (400 MHz, CDCl$_3$) $\delta_H$: 8.66 (d, J=2.0 Hz, 1H), 8.62 (d, J=2.0 Hz, 1H), 4.07-4.21 (m, 4H), 3.85-3.91 (m, 4H).

MS (ES$^+$) 393 (100%, [M+Na]$^+$), 391 (80%, [M+Na]$^+$).

v. (2E)-3-[4-Chloro-6-(morpholin-4-yl)-8-oxa-3,5,10-triazatricyclo [7.4.0.0$^{2,7}$]trideca-1(9),2(7),3,5,10,12-hexaen-12-yl]-N,N-dimethylprop-2-enamide To 12-bromo-4-chloro-6-(morpholin-4-yl)-8-oxa-3,5,10-triazatricyclo [7.4.0.0$^{2,7}$]trideca-1(9),2(7),3,5,10,12-hexaene (60 g, 0.15 mol, 1 eq) was added N,N-dimethylacrylamide (16.7 mL, 0.15 mol, 1 eq), PdCl$_2$(PPh$_3$)$_2$ (3.4 g, 4.5 mmol, 0.03 eq) and NaOAc (40 g, 0.45 mol, 3 eq) in DMF (1.2 L). The reaction was heated at 110° C. for 7 h. This process was repeated 3 times and batches combined. Once cooled down to rt, solvent was removed in vacuo and the resulting residue was partitioned between CH$_2$Cl$_2$ (6.5

L) and water (5.5 L). The phases were separated and the aqueous phase was extracted with CH$_2$Cl$_2$ (2×4 L). The combined organics were washed with brine (2×4 L), dried over MgSO$_4$, filtered and stripped. The resulting solid was slurried in EtOAc/heptane (1:1, 0.8 L) for 30 mins, filtered, washed and washed with EtOAc/heptane (1:1, 2×450 mL). Further drying in a vacuum oven at 40° C. yielded the desired product as an orange solid (203.0 g, 86%).

$^1$H NMR (400 MHz, CDCl$_3$) δ$_H$: 8.70 (s, 2H), 7.82 (d, J=15.6 Hz, 1H), 7.07 (d, J=15.6 Hz, 1H), 4.11-4.19 (m, 4H), 3.85-3.93 (m, 4H), 3.22 (s, 3H), 3.11 (s, 3H).

MS (ES$^+$) 388 (100%, [M+H]$^+$).

vi. 4-Chloro-6-(morpholin-4-yl)-8-oxa-3,5,10-triazatricyclo[7.4.0.0$^{2,7}$]trideca-1(9),2(7),3,5,10,12-hexaene-12-carbaldehyde (2E)-3-[4-chloro-6-(morpholin-4-yl)-8-oxa-3,5,10-triazatricyclo[7.4.0.0$^{2,7}$]trideca-1(9),2(7),3,5,10,12-hexaen-12-yl]-N,N-dimethylprop-2-enamide (124.0 g, 0.39 mol, 1 eq) was dissolved in THF (12.4 L) at 65° C. Once cooled to 35° C., water (4.1 L), NaIO$_4$ (205.4 g, 1.17 mol, 3 eq) and OsO$_4$ (2.5 wt % in $^t$BuOH, 80.3 mL, 2%) were added. The reaction was stirred at rt for 60 h. The reaction was cooled to 0-5° C., stirred for 30 mins then filtered. The solid was washed with water (545 mL) and pulled dry. The crude product was combined with two further batches (2×118.3 g scale) and slurried in water (6.3 L) for 30 mins at rt. The solids were filtered, washed with water (1.6 L) and pulled dry. Further drying in a vacuum oven yielded the desired product as a pink solid (260 g, 88%)

$^1$H NMR (400 MHz, CDCl$_3$:MeOD, 9:1) δ$_H$: 10.13 (s, 1H), 9.04 (d, J=2.0 Hz, 1H), 8.91 (d, J=2.0 Hz, 1H), 3.99-4.13 (m, 4H), 3.73-3.84 (m, 4H).

MS (ES$^+$) 351 (100%, [M+MeOH+H]$^+$).

vii. 4-(1H-Indol-4-yl)-6-(morpholin-4-yl)-8-oxa-3,5,10-triazatricyclo [7.4.0.0$^{2,7}$]trideca-1 (9),2,4,6,10,12-hexaene-12-carbaldehyde To 4-chloro-6-(morpholin-4-yl)-8-oxa-3,5,10-triazatricyclo[7.4.0.0$^{2,7}$]trideca-1(9),2(7),3,5,10,12-hexaene-12-carbaldehyde (164.4 g, 0.52 mol, 1 eq) was added indole-4-boronic acid pinacol ester (376.0 g, 1.55 mol, 3 eq), PdCl$_2$(PPh$_3$)$_2$ (72.0 g, 0.10 mol, 2 eq) and sodium carbonate (110.2 g, 1.04 mol, 2 eq) in dioxane (16.4 L)/water (5.8 L). Reaction mixture was refluxed for 1 h. It was then cooled to 60-70° C. Water (9.8 L), brine (4.9 L) and EtOAc (9.5 L) were added. The phases were separated and the aqueous phase extracted with EtOAc (3×9.5 L) at 60-65° C. The combined organics were dried over MgSO$_4$, filtered and stripped. The resulting solid was slurried in CH$_2$Cl$_2$ (4.75 L) for 30 mins, filtered, washed with CH$_2$Cl$_2$ (3×238 mL) and pulled dry. Further drying in a vacuum oven at 40° C. yielded Intermediate X as a yellow solid (135.7 g, 66%).

$^1$H NMR (300 MHz, CDCl$_3$) δ$_H$: 11.27 (br. s, 1H), 10.26 (s, 1H), 9.16 (d, J=2.3 Hz, 1H), 9.11 (d, J=2.3 Hz, 1H), 8.18 (d, J=7.5 Hz, 1H), 7.58-7.67 (m, 2H), 7.49 (t, J=2.8 Hz, 1H), 7.23 (t, J=7.7 Hz, 1H), 4.08-4.16 (m, 4H), 3.83-3.90 (m, 4H).

MS (ES$^+$) 432.0 (100%, [M+MeOH+H]$^+$).

Synthesis of Examples of the Present Invention

Example A 4-(1H-Indol-4-yl)-6-(morpholin-4-yl)-12-[(1S,4S)-2-oxa-5-azabicyclo [2.2.1]heptan-5-ylmethyl]-8-oxa-3,5,10-triazatricyclo[7.4.0.0$^{2,7}$]trideca-1(13),2(7),3,5,9,11-hexaene

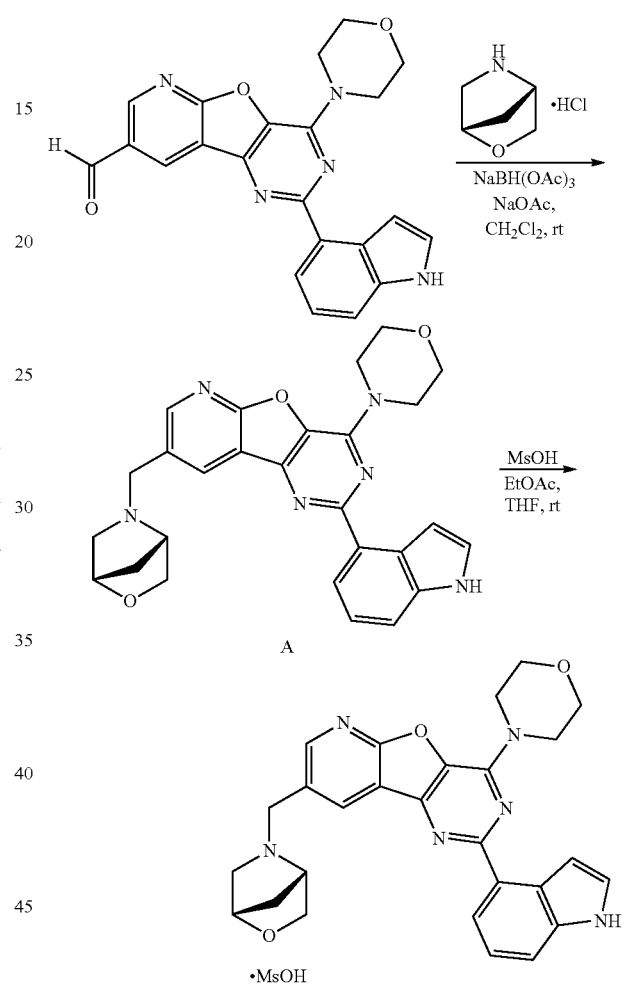

A

·MsOH

To a suspension of intermediate X (7.00 g, 17.53 mmol, 1 eq), (1S,4S)-2-oxa-5-azabicyclo [2.2.1]heptane hydrochloride (7.13 g, 52.58 mmol, 3 eq) and NaOAc (4.31 g, 52.58 mmol, 3 eq) in anhydrous CH$_2$Cl$_2$ (150 mL) was added NaBH(OAc)$_3$ (7.43 g, 35.06 mmol, 2 eq). The reaction mixture was stirred at rt overnight. Then, it was partitioned with 1N NaOH (100 mL) and extracted with CH$_2$Cl$_2$ (3×200 mL). The combined organic extracts were washed with brine (50 mL) then dried over MgSO$_4$ and the solvent was removed in vacuo. Purification by silica gel column chromatography with EtOAc/MeOH (1:0-7:1) yielded the product A as a white solid (6.02 g, 71%).

$^1$H NMR (300 MHz, CDCl$_3$) δ$_H$: 8.65 (d, J=2.1 Hz, 1H), 8.58 (d, J=2.1 Hz, 1H), 8.37 (br. s, 1H), 8.24 (dd, J=7.5, 0.9 Hz, 1H), 7.62 (td, J=2.6, 0.8 Hz, 1H), 7.53 (d, J=8.1 Hz, 1H), 7.37-7.41 (m, 1H), 7.31-7.37 (m, 1H), 4.47 (s, 1H), 4.22-4.30 (m, 4H), 4.18 (d, J=8.1 Hz, 1H), 3.98 (d, J=2.3 Hz, 2H), 3.91-3.97 (m, 4H), 3.70 (dd, J=7.9, 1.7 Hz, 1H), 3.53 (s, 1H), 2.94 (dd, J=10.0, 1.5 Hz, 1H), 2.64 (d, J=10.2 Hz, 1H), 1.97 (dd, J=9.8, 1.9 Hz, 1H), 1.80 (dt, J=9.8, 1.1 Hz, 1H).

MS (ES+) 483.1 (100%, [M+H]+).

4-(1H-Indol-4-yl)-6-(morpholin-4-yl)-12-[(1S,4S)-2-oxa-5-azabicyclo [2.2.1]heptan-5-ylmethyl]-8-oxa-3,5,10-triazatricyclo[7.4.0.0$^{2,7}$]trideca-1(13),2(7),3,5,9,11-hexaene; methanesulfonic acid A (5.98 g, 12.38 mmol, 1 eq) was dissolved in hot EtOAc (1 L) and THF (200 mL). Once cooled down to rt, a solution of MsOH (884 μL, 13.6 mmol, 1.1 eq) in EtOAc (5 mL) was added slowly. An instant yellow precipitate formed. The suspension was shaken vigorously for 10 s then left to stand at rt overnight. As solid settled, excess supernatant was decanted off (200 mL), then EtOAc was added (200 mL). The suspension was shaken again and left to stand for 1 h. This operation was repeated twice, then the solvent was removed in vacuo. The salt form of A was obtained as a yellow solid (6.50 g, 91%).

$^1$H NMR (300 MHz, DMSO-d$_6$) δ$_H$: 11.33 (br. s., 1H), 9.69-10.24 (m, 1H), 9.05 (d, J=2.1 Hz, 1H), 8.79-8.93 (m, 1H), 8.19 (d, J=7.5 Hz, 1H), 7.54-7.62 (m, 2H), 7.50 (t, J=2.7 Hz, 1H), 7.24 (t, J=7.7 Hz, 1H), 4.64-4.89 (m, 2H), 4.47-4.61 (m, 2H), 4.14 (m, 4H), 3.94-4.00 (m, 2H), 3.83-3.91 (m, 4H), 3.72-3.83 (m, 1H), 3.29-3.46 (m, 2H), 2.33 (s, 4H), 2.02-2.15 (m, 1H).

MS (ES+) 483.1 (100%, [M-MsOH+H]+).

Example B 4-(1H-Indol-4-yl)-6-(morpholin-4-yl)-12-{2-oxa-7-azaspiro[3.5]nonan-7-ylmethyl}-8-oxa-3,5,10-triazatricyclo[7.4.0.0$^{2,7}$]trideca-1(13), 2(7),3,5,9,11-hexaene

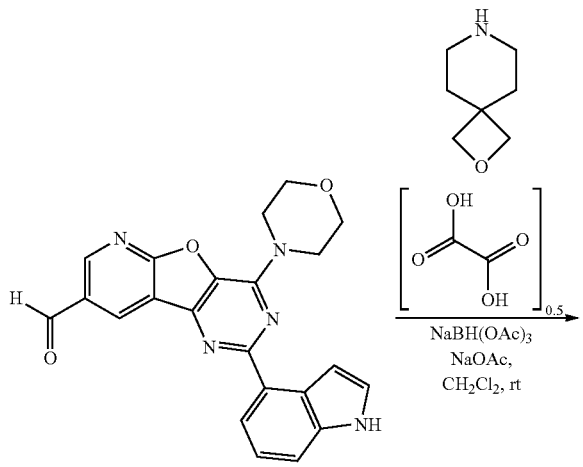
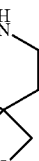
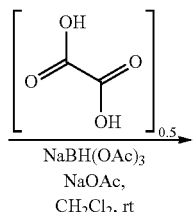

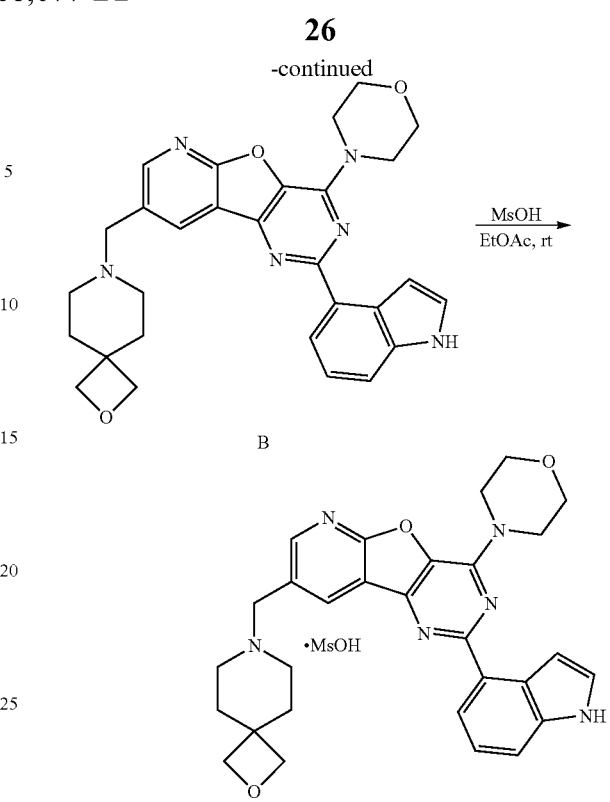

To a suspension of intermediate X (3.108 g, 7.78 mmol 1 eq), 2-oxa-7-azaspiro[3.5]nonane hemioxalate (4.02 g, 23.3 mmol, 3 eq) and NaOAc (1.91 g, 23.3 mmol, 3 eq) in anhydrous CH$_2$Cl$_2$ (280 mL) was added NaBH(OAc)$_3$ (3.30 g, 15.6 mmol, 2 eq). The reaction mixture was stirred at rt overnight. Then, it was partitioned with 1N NaOH (150 mL) and extracted with CH$_2$Cl$_2$ (2×100 mL). The combined organic extracts were washed with 50% brine (100 mL) then dried over MgSO$_4$ and the solvent was removed in vacuo. Purification by silica gel column chromatography with EtOAc/MeOH (1:0-8:1) yielded the product B as an off-white solid (3.154 g, 79%).

$^1$H NMR (300 MHz, CDCl$_3$) δ$_H$: 8.59 (d, J=2.1 Hz, 1H), 8.53 (d, J=1.9 Hz, 1H), 8.41 (br. s., 1H), 8.24 (dd, J=7.4, 0.8 Hz, 1H), 7.61 (t, J=2.3 Hz, 1H), 7.53 (d, J=8.1 Hz, 1H), 7.37-7.41 (m, 1H), 7.34 (t, J=7.9 Hz, 1H), 4.43 (s, 4H), 4.22-4.30 (m, 4H), 3.86-4.00 (m, 4H), 3.68 (s, 2H), 2.23-2.59 (m, 4H), 1.83-2.00 (m, 4H).

MS (ES+) 511.1 (100%, [M+H]+).

4-(1H-Indol-4-yl)-6-(morpholin-4-yl)-12-{2-oxa-7-azaspiro[3.5]nonan-7-ylmethyl}-8-oxa-3,5,10-triazatricyclo[7.4.0.0$^{2,7}$]trideca-1(13),2(7),3,5,9,11-hexaene; methanesulfonic acid To a solution of B (2.987 g, 5.854 mmol, 1 eq) in EtOAc (1.2 L, heat to 70° C. for 5 min to dissolve) at rt was added a solution of MsOH (590 μL, 6.14 mmol, 1.05 eq) in EtOAc (16 mL). A yellow precipitate formed instantly. The suspension was shaken vigorously for 20 s then left to stand at rt overnight. The excess supernatant was decanted off (600 mL), then EtOAc was added (500 mL). The suspension was shaken again and left to stand for 1 h before another 500 mL of excess supernatant was decanted off. The solvent was removed in vacuo to give the salt form of F as a yellow solid (3.230 g, 91%).

$^1$H NMR (300 MHz, DMSO-d$_6$) δ$_H$: 11.33 (br. s., 1H), 9.45 (br. s., 1H), 8.90 (d, J=1.9 Hz, 1H), 8.72 (d, J=1.9 Hz, 1H), 8.19 (d, J=7.3 Hz, 1H), 7.41-7.69 (m, 3H), 7.23 (t, J=7.8 Hz, 1H), 4.58 (d, J=3.8 Hz, 2H), 4.39 (s, 2H), 4.29 (s, 2H), 4.03-4.22 (m, 4H), 3.81-3.97 (m, 4H), 3.40 (d, J=12.1 Hz, 2H), 2.88-3.13 (m, 2H), 2.33 (s, 3H), 2.26 (d, J=13.9 Hz, 2H), 1.69-1.91 (m, 2H).

MS (ES$^+$) 511.1 (100%, [M-MsOH+H]$^+$).

Example C 4-(1H-Indol-4-yl)-6-(morpholin-4-yl)-12-{8-oxa-3-azabicyclo[3.2.1]octan-3-ylmethyl}-8-oxa-3,5,10-triazatricyclo [7.4.0.0$^{2,7}$]trideca-1(13),2(7),3,5,9,11-hexaene

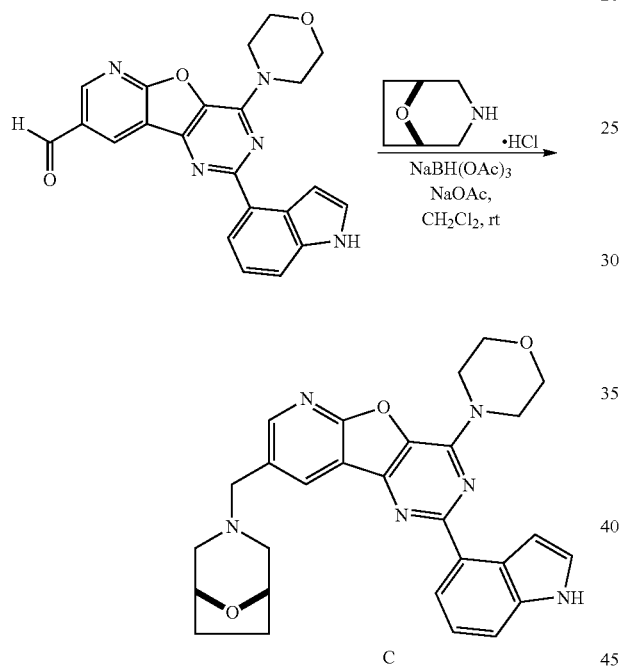

C

To a suspension of intermediate X (100 mg, 0.25 mmol, 1 eq), 8-oxa-3-azabicyclo [3.2.1]octane hydrochloride (112 mg, 0.75 mmol, 3 eq) and NaOAc (62 mg, 0.75 mmol, 3 eq) in anhydrous CH$_2$Cl$_2$ (10 mL) was added NaBH(OAc)$_3$ (106 mg, 0.50 mmol, 2 eq). The reaction mixture was stirred at rt overnight. Then, it was partitioned with 1N NaOH (10 mL), extracted with CH$_2$Cl$_2$ (3×10 mL). The combined organic extracts were washed with brine (10 mL) then dried over MgSO$_4$ and the solvent was removed in vacuo. Purification by silica gel column chromatography with EtOAc/MeOH (1:0-49:1) yielded the product C as an off white solid (116 mg, 93%).

$^1$H NMR (300 MHz, CDCl$_3$) δ$_H$: 8.56 (d, J=3.6 Hz, 2H), 8.35 (br. s., 1H), 8.24 (d, J=7.5 Hz, 1H), 7.58-7.66 (m, 1H), 7.51-7.57 (m, 1H), 7.31-7.44 (m, 2H), 4.30-4.38 (m, 2H), 4.23-4.30 (m, 4H), 3.89-4.01 (m, 4H), 3.68 (s, 2H), 2.61 (d, J=10.7 Hz, 2H), 2.40-2.52 (m, 2H), 1.96-2.09 (m, 2H), 1.83-1.95 (m, 2H).

MS (ES$^+$) 497.1 (100%, [M+H]$^+$).

Example D 4-(1H-Indol-4-yl)-12-({2-methyl-2,8-diazaspiro[4.5]decan-8-yl}methyl)-6-(morpholin-4-yl)-8-oxa-3,5,10-triazatricyclo [7.4.0.0$^{2,7}$]trideca-1(13),2(7),3,5,9,11-hexaene

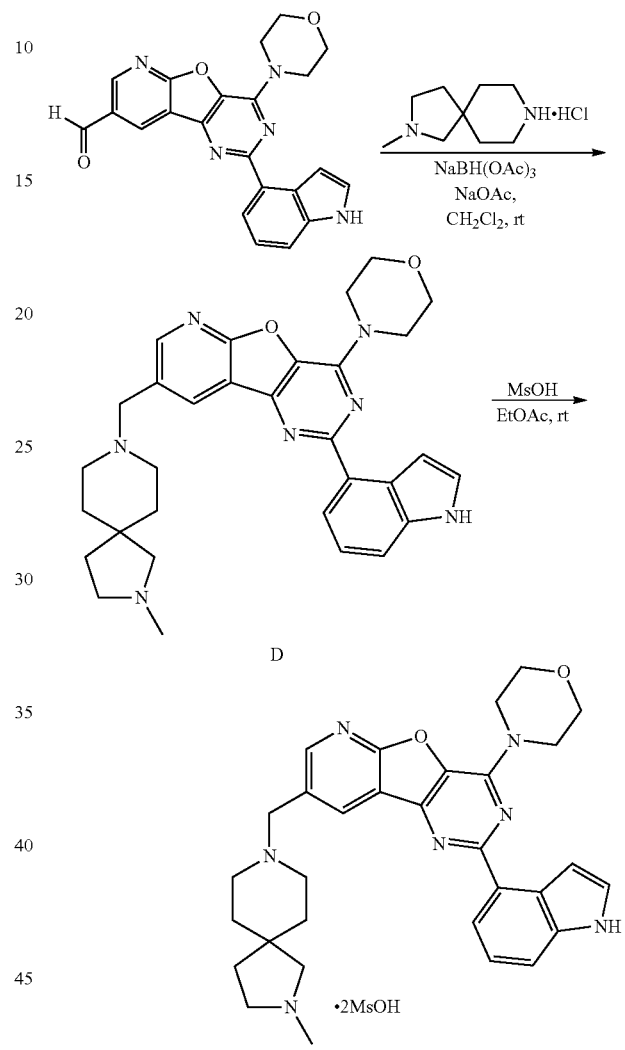

D

To a suspension of intermediate X (1.02 g, 2.55 mmol, 1 eq), 2-methyl-2,8-diazaspiro [4.5]decane hydrochloride (1.46 g, 7.66 mmol, 3 eq) and NaOAc (628 mg, 7.66 mmol, 3 eq) in anhydrous CH$_2$Cl$_2$ (100 mL) was added NaBH(OAc)$_3$ (1.08 g, 5.1 mmol, 2 eq). The reaction mixture was stirred at rt overnight. Then, it was partitioned with 1N NaOH (30 mL) and extracted with CH$_2$Cl$_2$ (3×50 mL). The combined organic extracts were washed with brine (10 mL) then dried over MgSO$_4$ and the solvent was removed in vacuo. Purification by silica gel column chromatography with CH$_2$Cl$_2$/MeOH (0:1-4:1) yielded the product D as a white solid (890 mg, 65%).

$^1$H NMR (300 MHz, CDCl$_3$) δ$_H$: 8.60 (d, J=2.1 Hz, 1H), 8.54 (d, J=2.1 Hz, 1H), 8.39 (br. s., 1H), 8.24 (dd, J=7.4, 0.8 Hz, 1H), 7.62 (t, J=2.3 Hz, 1H), 7.53 (d, J=8.1 Hz, 1H), 7.38 (t, J=2.8 Hz, 1H), 7.30-7.37 (m, 1H), 4.21-4.31 (m, 4H), 3.89-3.99 (m, 4H), 3.69 (s, 2H), 2.59 (t, J=6.8 Hz, 2H), 2.38-2.50 (m, 5H), 2.35 (s, 3H), 1.54-1.73 (m, 7H).

MS (ES$^+$) 538.2 (100%, [M+H]$^+$).

4-(1H-Indol-4-yl)-12-({2-methyl-2,8-diazaspiro[4.5]
decan-8-yl}methyl)-6-(morpholin-4-yl)-8-oxa-3,5,
10-triazatricyclo [7.4.0.0$^{2,7}$]trideca-1(13), 2(7),3,5,9,
11-hexaene; bis(methanesulfonic acid)

Compound D (821 mg, 1.52 mmol, 1 eq) was dissolved in hot EtOAc (400 mL). Once cooled down to rt, a solution of MsOH (218 μL, 3.36 mmol, 2.2 eq) in EtOAc (5 mL) was added slowly. An instant yellow precipitate formed. The suspension was shaken vigorously for 10 s then left to stand at rt overnight. As solid settled, excess supernatant was decanted off (200 mL), then EtOAc was added (200 mL). The suspension was shaken again and left to stand for 1 h. This operation was repeated twice, then the solvent was removed in vacuo. The salt form of D was obtained as a yellow solid (1.037 g, 93%).

$^1$H NMR (300 MHz, DMSO-d$_6$) δ$_H$: 11.32 (br. s., 1H), 9.46-10.03 (m, 2H), 8.93 (d, J=2.1 Hz, 1H), 8.76 (d, J=1.7 Hz, 1H), 8.19 (dd, J=7.4, 0.7 Hz, 1H), 7.53-7.60 (m, 2H), 7.50 (t, J=2.6 Hz, 1H), 7.24 (t, J=7.8 Hz, 1H), 4.63 (br. s., 2H), 4.10-4.20 (m, 4H), 3.82-3.91 (m, 5H), 3.54-3.77 (m, 2H), 3.36-3.51 (m, 2H), 3.05-3.25 (m, 3H), 2.89-3.03 (m, 1H), 2.80-2.89 (m, 3H), 2.36 (s, 6H), 2.02-2.17 (m, 1H), 1.65-1.95 (m, 4H).

MS (ES$^+$) 538.2 (100%, [M-2MsOH+H]$^+$).

Example E 4-(1H-Indol-4-yl)-12-({7-methyl-2,7-diazaspiro[4.4]
nonan-2-yl}methyl)-6-(morpholin-4-yl)-8-oxa-3,5,
10-triazatricyclo [7.4.0.0$^{2,7}$]trideca-1(13),2(7),3,5,9,
11-hexaene

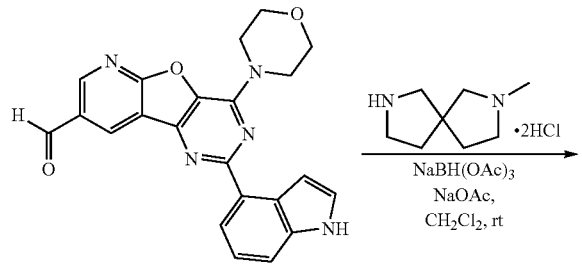

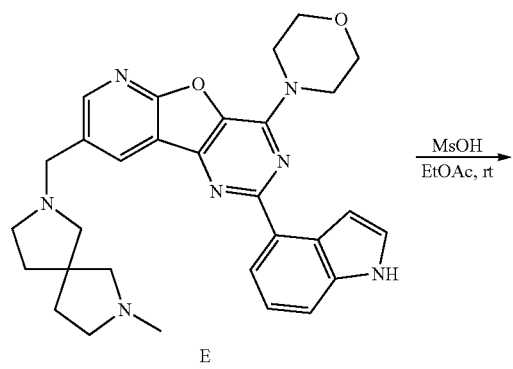

E

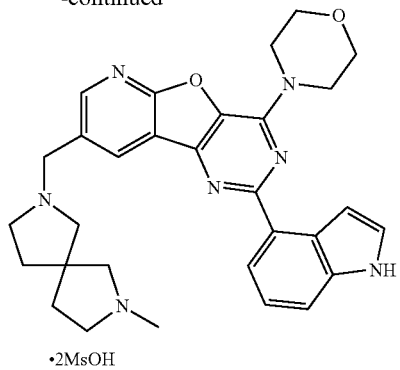

•2MsOH

To a suspension of intermediate X (250 mg, 0.63 mmol, 1 eq), 2-methyl-2,7-diazaspiro [4,4]nonane dihydrochloride (400 mg, 1.87 mmol, 3 eq) and NaOAc (305 mg, 3.70 mmol, 6 eq) in anhydrous CH$_2$Cl$_2$ (20 mL) was added NaBH (OAc)$_3$ (265 mg, 1.25 mmol, 2 eq). The reaction mixture was stirred at rt overnight. Then, it was partitioned with 1N NaOH (10 mL), extracted with CH$_2$Cl$_2$ (3×10 mL) and EtOAc (10 mL). The combined organic extracts were washed with brine (10 mL) then dried over MgSO$_4$ and the solvent was removed in vacuo. Purification by silica gel column chromatography with CH$_2$Cl$_2$/MeOH (0:1-4:1) yielded the product E as a white solid (169 mg, 52%).

$^1$H NMR (300 MHz, CDCl$_3$) δ$_H$: 8.58 (d, J=2.1 Hz, 1H), 8.53 (d, J=2.1 Hz, 1H), 8.48 (br. s., 1H), 8.23 (dd, J=7.4, 0.8 Hz, 1H), 7.63 (t, J=2.2 Hz, 1H), 7.53 (d, J=7.9 Hz, 1H), 7.39 (t, J=2.7 Hz, 1H), 7.29-7.36 (m, 1H), 4.21-4.30 (m, 4H), 3.89-3.99 (m, 4H), 3.72-3.85 (m, 2H), 2.49-2.83 (m, 8H), 2.45 (s, 3H), 1.81-2.06 (m, 4H).

MS (ES$^+$) 524.1 (100%, [M+H]$^+$).

4-(1H-Indol-4-yl)-12-({7-methyl-2,7-diazaspiro[4.4]
nonan-2-yl}methyl)-6-(morpholin-4-yl)-8-oxa-3,5,
10-triazatricyclo [7.4.0.0$^{2,7}$]trideca-1(13),2(7),3,5,9,
11-hexaene; bis(methanesulfonic acid)

Compound E (129 mg, 0.25 mmol, 1 eq) was dissolved in hot EtOAc (50 mL). Once cooled down to rt, a solution of MsOH (35 μL, 0.54 mmol, 2.2 eq) in EtOAc (2 mL) was added slowly. An instant yellow precipitate formed. The suspension was shaken vigorously for 10 s then left to stand at rt overnight. As solid settled, excess supernatant was decanted off (20 mL), then EtOAc was added (20 mL). The suspension was shaken again and left to stand for 1 h. This operation was repeated twice, then the solvent was removed in vacuo. The salt form of E was obtained as a yellow solid (173 mg, 98%).

$^1$H NMR (300 MHz, DMSO-d$_6$) δ$_H$: 11.33 (br. s., 1H), 10.39 (br. s., 1H), 9.72-10.12 (m, 1H), 8.73-9.09 (m, 2H), 8.19 (d, J=7.5 Hz, 1H), 7.41-7.63 (m, 3H), 7.24 (t, J=7.8 Hz, 1H), 4.53-4.87 (m, 2H), 4.10-4.22 (m, 4H), 3.79-3.93 (m, 4H), 3.32-3.77 (m, 6H), 2.99-3.29 (m, 2H), 2.78-2.89 (m, 3H), 2.36 (s, 6H), 1.87-2.22 (m, 3H).

MS (ES$^+$) 524.5 (100%, [M-2MsOH+H]$^+$).

Example F 4-(1H-Indol-4-yl)-6-(morpholin-4-yl)-12-[(1R,4R)-2-oxa-5-azabicyclo[2.2.1]heptan-5-ylmethyl]-8-oxa-3,5,10-triazatricyclo[7.4.0.0$^{2,7}$]trideca-1(13),2(7),3,5,9,11-hexaene

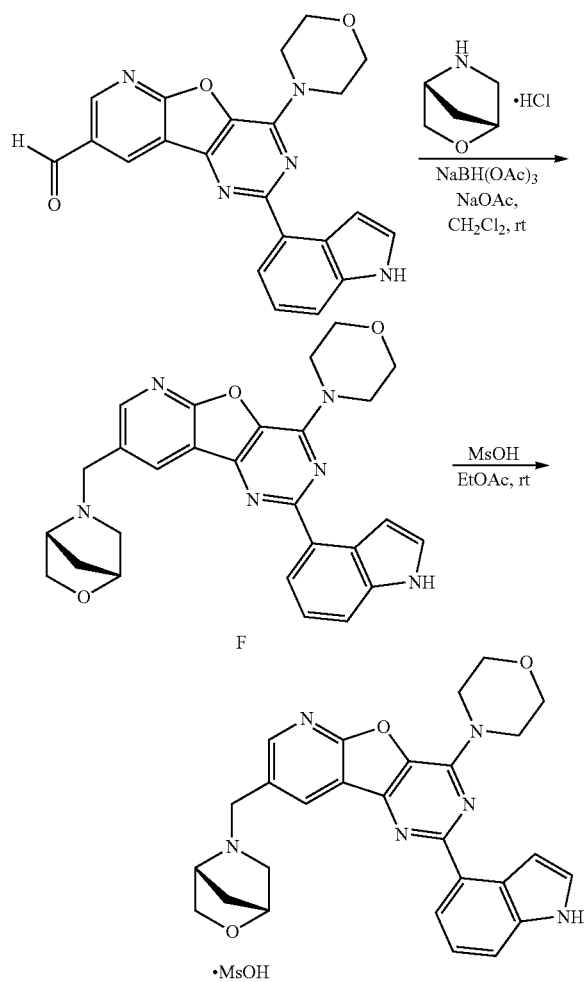

To a suspension of intermediate X (200 mg, 0.50 mmol, 1 eq), (1R,4R)-2-oxa-5-azabicyclo [2.2.1]heptane hydrochloride (204 mg, 1.50 mmol, 3 eq) and NaOAc (123 mg, 1.5 mmol, 3 eq) in anhydrous CH$_2$Cl$_2$ (10 mL) was added NaBH(OAc)$_3$ (160 mg, 0.76 mmol, 2 eq). The reaction mixture was stirred at rt overnight. Then, it was partitioned with 1N NaOH (20 mL) and extracted with CH$_2$Cl$_2$ (3×20 mL). The combined organic extracts were passed through a phase separator and the solvent was removed in vacuo. Purification by silica gel column chromatography with EtOAc/MeOH (1:0-9:1) yielded the product F as a white solid (141.1 mg, 59%).

$^1$H NMR (400 MHz, CDCl$_3$) δ$_H$: 8.64 (d, J=2.1 Hz, 1H), 8.57 (d, J=2.1 Hz, 1H), 8.35 (br. s., 1H), 8.23 (dd, J=7.5, 0.9 Hz, 1H), 7.62 (m, 1H), 7.53 (d, J=8.1 Hz, 1H), 7.36-7.39 (m, 1H), 7.31-7.36 (m, 1H), 4.46 (s, 1H), 4.25 (m, 4H), 4.18 (d, J=8.1 Hz, 1H), 3.97 (d, J=2.3 Hz, 2H), 3.93-3.97 (m, 4H), 3.68 (dd, J=7.9, 1.7 Hz, 1H), 3.53 (s, 1H), 2.93 (dd, J=10.0, 1.5 Hz, 1H), 2.62 (d, J=10.2 Hz, 1H), 1.95 (dd, J=9.8, 1.9 Hz, 1H), 1.79 (dt, J=9.8, 1.1 Hz, 1H).

MS (ES$^+$) 483.1 (100%, [M+H]$^+$).

4-(1H-Indol-4-yl)-6-(morpholin-4-yl)-12-[(1R,4R)-2-oxa-5-azabicyclo [2.2.1]heptan-5-yl methyl]-8-oxa-3,5,10-triazatricyclo[7.4.0.0$^{2,7}$]trideca-1(13),2(7),3,5,9,11-hexaene; methanesulfonic acid Compound F (141 mg, 0.29 mmol, 1 eq) was dissolved in hot EtOAc (100 mL) then treated with 0.87 ml of a 0.308M MsOH solution in EtOAc under vigorously swirling. The mixture was set aside overnight. The excess supernatant was decanted (using a small Pasteur pipette) and more EtOAc (50 ml) was added. The suspension was once again shaken vigorously then left to stand at rt overnight. The excess supernatant was once more decanted and the solvent was removed in vacuo. The resulting solid was dried in a vacuum oven at 40° C. The salt form of F was obtained as a yellow solid (160 mg, 95%).

$^1$H NMR (400 MHz, DMSO-d$_6$) δ$_H$: 11.33 (br. s., 1H), 9.65-10.16 (m, 1H), 9.05 (d, J=2.0 Hz, 1H), 8.83-8.90 (m, 1H), 8.20 (d, J=7.3 Hz, 1H), 7.58-7.61 (m, 1H), 7.56 (d, J=7.8 Hz, 1H), 7.51 (t, J=2.8 Hz, 1H), 7.23 (t, J=7.7 Hz, 1H), 4.82 (dd, J=13.1, 4.5 Hz, 1H), 4.65-4.76 (m, 1H), 4.50-4.59 (m, 2H), 4.11-4.19 (m, 4H), 3.99 (d, J=9.6 Hz, 1H), 3.88 (t, J=4.5 Hz, 4H), 3.78 (dd, J=9.5, 1.4 Hz, 1H), 3.31-3.38 (m, 2H), 2.52-2.57 (m, 1H), 2.30 (s, 3H), 2.02-2.18 (m, 1H).

MS (ES$^+$) 483.2 (100%, [M-MsOH+H]$^+$).

Example G 4-(1H-indol-4-yl)-6-(morpholin-4-yl)-12-{6-oxa-1-azaspiro[3.3]heptan-1-ylmethyl}-8-oxa-3,5,10-triazatricyclo[7.4.0.0$^{2,7}$]trideca-1(13), 2(7), 3,5,9,11-hexaene

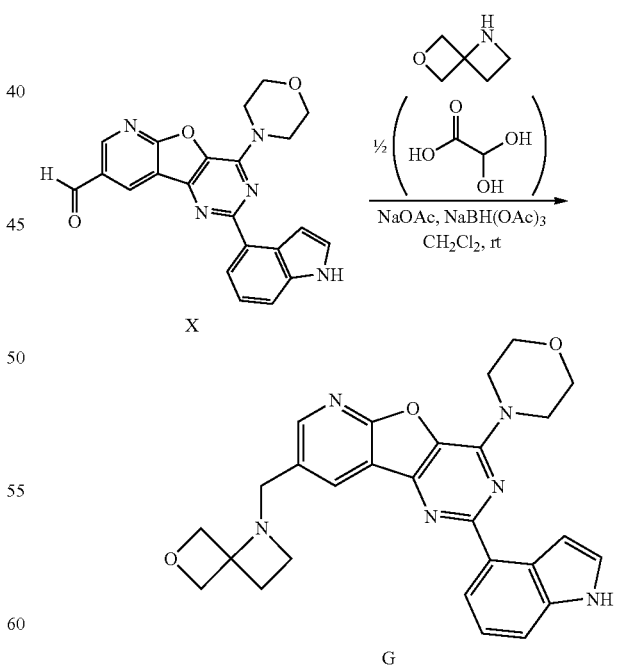

Intermediate X (125 mg, 0.31 mmol), 6-oxa-1-azaspiro [3.3]heptane hemioxalate (134 mg, 0.93 mmol, 3 eq) and NaOAc (76 mg, 0.93 mmol, 3 eq) were suspended in CH$_2$Cl$_2$ (16 mL) at rt. The mixture was stirred for 15 mins then NaBH(OAc)$_3$ (131 mg, 0.62 mmol, 2 eq) was added. The resulting suspension was stirred at rt overnight. The reaction mixture was then partitioned with 0.5 N NaOH (8 mL) and extracted with CH$_2$Cl$_2$ (2×10 mL). The combined organics were washed with 50% brine (5 mL) then dried over MgSO$_4$ and the solvent was removed in vacuo. The residue was dissolved in DMSO (2 mL) and purified by basic preparative LCMS to yield G as a white solid (48 mg, 32%).

$^1$H NMR (DMSO-d$_6$) $\delta_H$: 11.30 (br s, 1H), 8.62 (s, 2H), 8.18 (d, J=7.6 Hz, 1H), 7.51-7.58 (m, 2H), 7.46-7.51 (m, 1H), 7.22 (t, J=7.7 Hz, 1H), 4.89 (d, J=7.6 Hz, 2H), 4.55 (d, J=7.3 Hz, 2H), 4.08-4.17 (m, 4H), 4.03 (s, 2H), 3.81-3.91 (m, 4H), 3.03 (t, J=6.7 Hz, 2H), 2.32 (t, J=6.7 Hz, 2H).

MS (ES$^+$) 483.3 (100%, [M+H]$^+$).

Biological Data

Fold form selectivity inhibition data against class I PI3K isoforms, as determined using a HTRF biochemical assay conducted at Reaction Biology Corp., is listed below.

| Example | Fold IC$_{50}$ | | | |
|---|---|---|---|---|
| | p110β/p110α | p110β/p110γ | p110δ/p110α | p110δ/p110γ |
| A | * | ** | * | ** |
| B | ** | ** | ** | ** |
| C | * | ** | ** | ** |
| D | ** | ** | ** | ** |
| E | ** | ** | ** | ** |
| F | * | * | ** | ** |
| G | * | ** | ** | ** |

Key:
* = ≥10x ≥ 50x;
** = >50x

Rodent Pharmacokinetic Comparative Data

Disclosed compounds have increased bioavailability and/or reduced clearance (data below for mice).

Example A

The following protocol was used to determine oral bioavailability and clearance, and the results are shown below:
Species=male mouse;
Strain=CD1;
n=3 male mice per time point per route;
Terminal blood sampling at 8 time points (5 min, 10 min, 0.5 hr, 1 hr, 3 hr, 6 hr, 8 hr and, 24 hr);
Collection of plasma, bio-analysis and report of pharmacokinetic parameters.
Formulation: 10% DMSO, 90% Saline
Dosing: 10 mg/kg P.O. and 5 mg/kg I.V.
Plasma PK Summary:

| | Value - Mesylate Salt |
|---|---|
| Parameters - IV, 5 mg/kg | |
| t$_{1/2}$ (hr) | 1.3 |
| T$_{max}$ (hr) | 0.08 |
| C$_{max}$ (ng/mL) | 2640 |
| AUC$_{last}$ (hr*ng · mL) | 3905 |
| AUC$_{all}$ (hr*ng/mL) | 3905 |
| AUC$_{inf}$ (hr*ng/mL) | 3946 |
| Clearance (mL/hr/Kg) | 1267 |
| Vd (mL/Kg) | 2441 |

| | Value - Mesylate Salt |
|---|---|
| Parameters - PO, 10 mg/kg | |
| t$_{1/2}$ (hr) | 1.3 |
| T$_{max}$ (hr) | 1.00 |
| C$_{max}$ (ng/mL) | 1973 |
| AUC$_{last}$ (hr*ng/mL) | 5625 |
| AUC$_{all}$ (hr*ng/mL) | 5625 |
| AUC$_{inf}$ (hr* ng/mL) | 5822 |
| F | 73.77% |

Example A

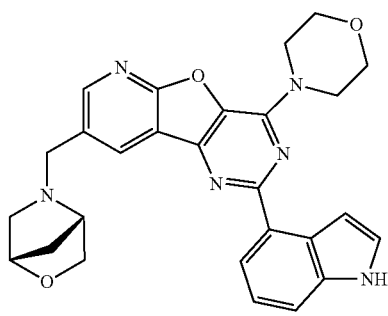 [SMILES: c1cc(-c2nc(N3CCOCC3)c3oc4ncc(CN5C[C@@H]6C[C@H]5CO6)cc4c3n2)c2cc[nH]c2c1]

Oral bioavailability (F)=74%
Clearance=21 mL/min/kg

Example B

The following protocol was used to determine oral bioavailability and clearance, and the results are shown below:
Species=male mouse;
Strain=Balb/c;
18 male mice were divided into two groups Group 1 (3 mg/kg; I.V.), Group 2 (10 mg/kg; P.O.) with each group comprising of nine mice;
Blood samples (approximately 60 μL) were collected from retro orbital plexus under light isoflurane anesthesia such that the samples were obtained at pre-dose, 0.08, 0.25, 0.5, 1, 2, 4, 8 and 24 hr (I.V.) and pre-dose, 0.25, 0.5, 1, 2, 4, 6, 8 and 24 hr (P.O.);
The blood samples were collected from a set of three mice at each time point in labeled micro centrifuge tube containing K2EDTA as anticoagulant;
Plasma samples were separated by centrifugation of whole blood and stored below −70° C. until bioanalysis;
All samples were processed for analysis by protein precipitation using acetonitrile (ACN) and analyzed with fit for purpose LC/MS/MS method (LLOQ: 2.02 ng/mL);
Pharmacokinetic parameters were calculated using the non-compartmental analysis tool of Phoenix WinNonlin (Version 6.3).

Formulation:
Animals in Group 1 were administered intravenously with Example B solution formulation in 20% Propylene Glycol, 50% of PEG 400 and 30% of (20% HPβCD in water) via tail vein at a dose of 3 mg/kg.
Animals in Group 2 were administered with oral solution formulation of Example B in 20% Propylene Glycol, 50% of PEG 400 and 30% of (20% HPβCD in water) at a dose of 10 mg/kg;
Dosing: 10 mg/kg P.O. and 3 mg/kg I.V.

Plasma PK Summary:

| | Value - Mesylate Salt |
|---|---|
| Parameters - IV, 3 mg/kg | |
| $t_{1/2}$ (hr) | 1.23 |
| $C_{max}$ (ng/mL) | 621.42 |
| $AUC_{last}$ (hr*ng · mL) | 1512.20 |
| $AUC_{inf}$ (hr*ng/mL) | 1512.20 |
| Clearance (mL/hr/Kg) | 1983.6 |
| Vss (L/Kg) | 5.51 |
| Parameters - PO, 10 mg/kg | |
| $T_{max}$ (hr) | 1.00 |
| $C_{max}$ (ng/mL) | 779.58 |
| $AUC_{last}$ (hr*ng/mL) | 3725.56 |
| $AUC_{inf}$ (hr* ng/mL) | 4103.86 |
| F | 74% |

Example B

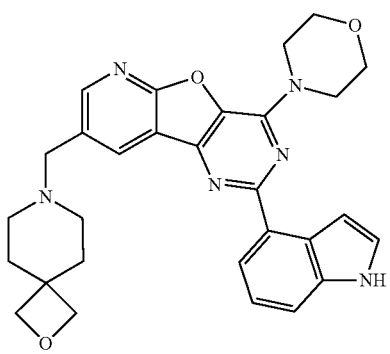 [SMILES: c1cc(-c2nc(N3CCOCC3)c3oc4ncc(CN5CCC6(CC5)COC6)cc4c3n2)c2cc[nH]c2c1]

Oral bioavailability (F)=74%
Clearance=33 mL/min/kg

Example G

The following protocol was used to determine oral bio-availability and clearance, and the results are shown below:
Species=male mouse;
Strain=Balb/c;
18 male mice were divided into two groups Group 1 (3 mg/kg; I.V.), Group 2 (10 mg/kg; P.O.) with each group comprising of nine mice;
Blood samples (approximately 60 µL) were collected from retro orbital plexus under light isoflurane anesthesia such that the samples were obtained at pre-dose, 0.08, 0.25, 0.5, 1, 2, 4, 8 and 24 hr (I.V.) and pre-dose, 0.25, 0.5, 1, 2, 4, 6, 8 and 24 hr (P.O.);
The blood samples were collected from set of three mice at each time point in labeled micro centrifuge tube containing K2EDTA as anticoagulant;
Plasma samples were separated by centrifugation of whole blood and stored below −70° C. until bioanalysis;
All samples were processed for analysis by protein precipitation using acetonitrile (ACN) and analyzed with fit for purpose LC/MS/MS method (LLOQ: 2.47 ng/mL);
Pharmacokinetic parameters were calculated using the non-compartmental analysis tool of Phoenix WinNonlin (Version 6.3).

Formulation:
Animals in Group 1 were administered intravenously with Example G solution formulation in 5% NMP, 5% solutol HS-15 in 90% HPβCD solution (20% HPβCD in RO water) at 3 mg/kg dose.
Animals in Group 2 were administered orally with 10 mg/kg solution formulation of Example G in 5% NMP, 5% solutol HS-15 in 90% HPβCD solution (20% HPβCD in RO water)
Dosing: 10 mg/kg P.O. and 3 mg/kg I.V.

Plasma PK Summary:

| | Value - Mesylate Salt |
|---|---|
| Parameters - IV, 3 mg/kg | |
| $t_{1/2}$ (hr) | 0.59 |
| $C_{max}$ (ng/mL) | 2205.80 |
| $AUC_{last}$ (hr*ng · mL) | 1918.37 |
| $AUC_{inf}$ (hr*ng/mL) | 1935.24 |
| Clearance (mL/hr/Kg) | 1550.4 |
| Vss (L/Kg) | 1.25 |
| Parameters - PO, 10 mg/kg | |
| $T_{max}$ (hr) | 0.25 |
| $C_{max}$ (ng/mL) | 833.35 |
| $AUC_{last}$ (hr*ng/mL) | 1892.53 |
| $AUC_{inf}$ (hr* ng/mL) | 2144.97 |
| F | 30% |

Example G

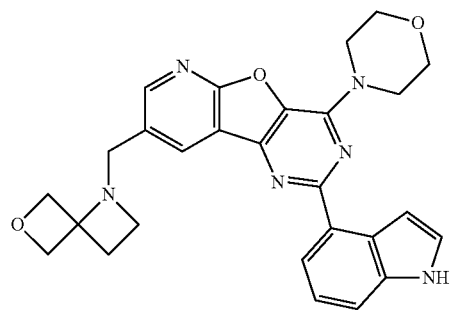 [SMILES: c1cc(-c2nc(N3CCOCC3)c3oc4ncc(CN5CCC56COC6)cc4c3n2)c2cc[nH]c2c1]

Oral bioavailability (F)=30%
Clearance=26 mL/min/kg

Comparative Example (Example I in WO2011/021038)

The following protocol was used to determine oral bio-availability and clearance, and the results are shown below:
Species=male mouse;
Strain=CD1;
n=3 male mice per time point per route;
Terminal blood sampling at 8 time points (5 min, 10 min, 0.5 hr, 1 hr, 3 hr, 6 hr, 8 hr and, 24 hr);
Collection of plasma, bio-analysis and report of pharmacokinetic parameters.
Formulation: 10% DMSO, 90% Saline
Dosing: 10 mg/kg P.O. and 5 mg/kg I.V.

Plasma PK Summary:

|  | Value - Mesylate Salt | Value - HCl Salt |
|---|---|---|
| Parameters - IV, 5 mg/kg | | |
| $t_{1/2}$ (hr) | 1.6 | 7.6 |
| $T_{max}$ (hr) | 0.08 | 0.08 |
| $C_{max}$ (ng/mL) | 1618 | 1712 |
| $AUC_{last}$ (hr*ng·mL) | 1245 | 1479 |
| $AUC_{all}$ (hr*ng/mL) | 1245 | 1479 |
| $AUC_{inf}$ (hr*ng/mL) | 1261 | 1515 |
| Clearance (mL/hr/Kg) | 3966 | 3300 |
| Vd (mL/Kg) | 4601 | 10063 |
| Parameters - PO, 10 mg/kg | | |
| $t_{1/2}$ (hr) | 1.9 | 1.8 |
| $T_{max}$ (hr) | 1.0 | 1.0 |
| $C_{max}$ (ng/mL) | 212 | 322 |
| $AUC_{last}$ (hr*ng/mL) | 657 | 849 |
| $AUC_{all}$ (hr*ng/mL) | 657 | 849 |
| $AUC_{inf}$ (hr*ng/mL) | 700 | 896 |
| F | 27.8% | 29.6% |

Example I in WO2011/021038
(Comparative)—Mesylate Salt Form

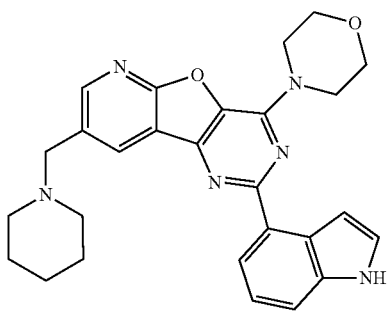 [SMILES: c1cc(-c2nc(N3CCOCC3)c3oc4ncc(CN5CCCCC5)cc4c3n2)c2cc[nH]c2c1]

Oral bioavailability (F)=28%
Clearance=66 mL/min/kg

SUMMARY

| Compound | Oral Bioavailability (F) | Clearance (mL/min/kg) |
|---|---|---|
| Example A | 74 | 21 |
| Example B | 74 | 33 |
| Example G | 30 | 26 |
| Example I from WO2011/021038 (comparative) | 28 | 66 |

Combination Data
Introduction

Data for an in vitro combination study are provided below.

The effects on the growth of a panel of cancer cell lines of a PI3K-p110β/δ inhibitor which is Example A as disclosed herein (referred to in this experimental section as "Compound A") alone or in combination with the following agents were tested:
i. PS-341 (Bortezomib), a proteasome inhibitor
ii. LY2584702, a p70S6K inhibitor
iii. PCI-32765 (Ibrutinib), a BTK and Tec family inhibitor
iv. AZD6244 (Selumetinib), a MEK1 inhibitor Materials and Methods
Proliferation Assay 21 cell lines were tested in parallel 22RV1, 786O, A375, DLD1, DU145, EJ28, GRANTA-519, KASUMI-1, L-363, MDA-MB-231, MDA-MB-468, MINO, PANC1, PC-3, SF268, SK-MEL-28, SU-DHL-6, U87MG, UMUC3, UO31 and WSU-NHL. Cell growth and treatment were performed in CELLSTAR® 96-well microtitre plates (Greiner Bio-One, Germany). Cells were harvested from exponential phase cultures by trypsinization and plated in 190 μL of media at optimal seeding densities. 48 hours later, cells were treated with media containing 10 μL of 20× concentrated compound (resulting in a final DMSO concentration of 0.1%). The cells were allowed to grow at 37° C. for 72 hours. In addition, control plates with cells were analyzed after 48 hours ($T_z$, at time zero i.e. before treatment). Cell viability was determined using a sulforhodamine B (SRB) total protein staining assay. Briefly—after treatment, media was aspirated and cells were fixed to the surface by addition of 10% TCA. After an hour of incubation at 4° C. plates were washed two times with 400 μL of deionized water and dried. Cells were then stained with 100 μL of 0.04% wt/v SRB. The plates were incubated at room temperature for at least 30 min and washed six times with 1% acetic acid to remove unbound stain. The plates were left to dry at room temperature and bound SRB was solubilized with 100 μL of 10 mM Tris base. Measurement of optical density was performed at 492, 520, and 560 nm by using a Victor-2 plate reader (Perkin Elmer).

Data Analysis

Average background (derived from plates and wells containing medium without cells) optical density was subtracted from the appropriate control values (containing cells without addition of a drug), from values representing the cells treated with agent, and from values of wells containing cells at time zero. Non-linear curve fitting calculations were performed using algorithms and visualization tools developed at Oncolead. The calculations included the dose response curves with the best approximation line, a 95% confidence interval for the 50% effect ($IC_{50}$) and the concentration of test agents giving a % T/C value of 50%, or 50% growth inhibition ($IC_{50}$), and a % T/C value of 10%, or 90% growth inhibition ($IC_{90}$). The $IC_{50}$, $IC_{90}$, $GI_{50}$, $GI_{90}$ and TGI values were computed automatically. All values were log 10-transformed for z-score analysis performed using proprietary software developed at Oncolead integrated as a database analysis tool. The screening was designed to identify potential synergistic combinations using CI, Bliss and highest single agent (HSA) indexation. Data are plotted as Loewe additivity isobolograms or Bliss independence calculations.

Results
Compound A—Bortezomib Combination

The effects on the growth of cancer cells of the PI3K-p110β/δ inhibitor Compound A alone or in combination with the proteasome inhibitor bortezomib was tested in a panel of 21 cancer cell lines in a matrix dose response study. The averaged Bliss independence (across all concentrations tested) suggested little or no synergy or potential antagonism was apparent in the cell lines tested.

Compound A—LY2584702 Combination

The effects on the growth of cancer cells of the PI3K-p110β/δ inhibitor Compound A alone or in combination with the p70S6K inhibitor LY2584702 was tested in a panel of 21 cancer cell lines in a matrix dose response study. The averaged Bliss independence (across all concentrations tested) suggested a limited synergistic effect on the growth inhibition of MINO, U87MG, UO31 and SK-MEL-28 cells when combining Compound A & LY2584702. No synergy or potential antagonism was observed in the other cell lines tested.

Compound A—Ibrutinib Combination

The effects on the growth of cancer cells of the PI3K-p110β/δ inhibitor Compound A alone or in combination with the BTK inhibitor ibrutinib was tested in a panel of 21 cancer cell lines in a matrix dose response study. The averaged Bliss independence (across all concentrations tested) suggested a synergistic effect on the growth inhibition of MINO, SU-DHL-6 and WSU-NHL haematological cell lines and further a synergistic effect on the growth inhibition of 786-O, DU-145, MDA-MB-468, and DLD1 solid tumor cells when combining Compound A & ibrutinib. No synergy or potential antagonism was observed in the other cell lines tested.

Compound A Selumetinib Combination

The effects on the growth of cancer cells of the PI3K-p110β/δ inhibitor Compound A alone or in combination with the MEK inhibitor selumetinib was tested in a panel of 21 cancer cell lines in a matrix dose response study. The averaged Bliss independence (across all concentrations tested) suggested a synergistic effect on the growth inhibition of EJ28, DU-145, UO31, SK-MEL-28, 786-O, WSU-NHL, MDA-MB-231 and PANC1 cells when combining Compound A & selumetinib. No synergy or potential antagonism was observed in the other cell lines tested.

The invention claimed is:

1. A method of treating a cancer selected from the group consisting of chronic myelogenous leukaemia, acute myeloid leukaemia, lymphoma, and solid tumours in a patient in need thereof comprising administering to the patient a therapeutically effective amount of at least one compound of Formula I:

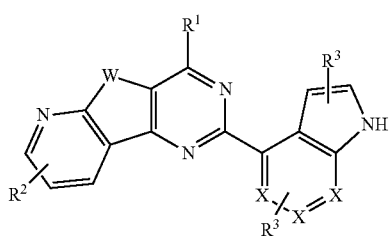

(I)

or a pharmaceutically acceptable salt thereof, wherein:
W is selected from the group consisting of O, N—H, N—($C_1$-$C_{10}$ alkyl) and S;
each X is independently CH or N;
$R^1$ is a 5 to 7-membered saturated or unsaturated heterocycle containing at least 1 heteroatom selected from N and O;
$R^2$ is LY;
each L is selected from the group consisting of a direct bond, $C_1$-$C_{10}$ alkylene, $C_2$-$C_{10}$ alkenylene, and $C_2$-$C_{10}$ alkynylene;
Y is a fused, bridged or spirocyclic non-aromatic 5-12 membered heterocycle containing up to 4 heteroatoms selected from N or O;
wherein any aforementioned heterocycle may be optionally substituted with up to three substituents selected from the group consisting of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, acyl, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl, and bis $C_1$-$C_3$-alkyl aminosulfonyl; and
each $R^3$ is independently selected from the group consisting of H, $C_1$-$C_{10}$ alkyl, halogen, fluoro $C_1$-$C_{10}$ alkyl, O—$C_1$-$C_{10}$ alkyl, NH—$C_1$-$C_{10}$ alkyl, S—$C_1$-$C_{10}$ alkyl, O-fluoro $C_1$-$C_{10}$ alkyl, NH-acyl, NH—C(O)—NH—$C_1$-$C_{10}$ alkyl, C(O)—NH—$C_1$-$C_{10}$ alkyl, aryl, and heteroaryl;
and at least one second agent selected from the group consisting of bortezomib, LY2584702, ibrutinib, and selumetinib.

2. A method according to claim 1, wherein the administration is separate, sequential or simultaneous.

3. The method according to claim 1, wherein $R^1$ is represented by any of the following structures:

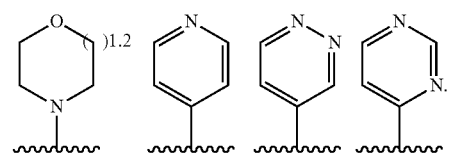

4. The method according to claim 1, wherein $R^1$ is morpholine.

5. The method according to claim 1, wherein W is O or S.

6. The method according to claim 1, wherein W is O.

7. The method according to claim 1, wherein X is CH.

8. The method according to claim 1, wherein $R^3$ is H.

9. The method according to claim 1, wherein L is $C_1$-$C_{10}$ alkylene.

10. The method according to claim 1, wherein Y contains one or two heteroatoms.

11. The method according to claim 1, wherein Y is selected from:

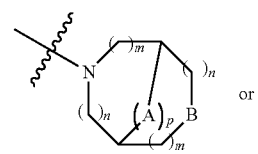

Formula A or

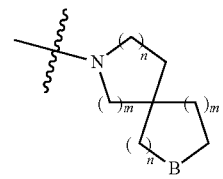

Formula B wherein:
A is selected from the group consisting of O, S, $NR^4$, $C_1$-$C_3$ alkylene, $C_2$-$C_3$ alkenylene, and $C_2$-$C_3$ alkynylene;
B is selected from the group consisting of $NR^4$, O, and $CH_2$;

wherein R⁴ is selected from the group consisting of H, $C_1$-$C_{10}$ alkyl, $C_2$-$C_{10}$ alkenyl, and $C_2$-$C_{10}$ alkynyl;

wherein the aforementioned $C_1$-$C_3$ alkylene, $C_2$-$C_3$ alkenylene, $C_2$-$C_3$ alkynylene, $C_1$-$C_{10}$ alkyl, $C_2$-$C_{10}$ alkenyl, or $C_2$-$C_{10}$ alkynyl may be optionally substituted with up to three substituents selected from the group consisting of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, acyl, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —SO₃H, $C_1$-$C_3$ alkylsulfonyl, aminosulfonyl, mono $C_1$-$C_3$ alkyl aminosulfonyl, and bis $C_1$-$C_3$-alkyl aminosulfonyl;

p is selected from 0 and 1;

each m is independently selected from 0, 1, and 2; and each n is independently selected from 1, 2, and 3.

12. The method according to claim 11, wherein A is O or $C_1$-$C_3$ alkylene.

13. The method according to claim 11, wherein B is O or CH₂.

14. The method according to claim 1, wherein the compound of formula (I) is selected from the group consisting of:

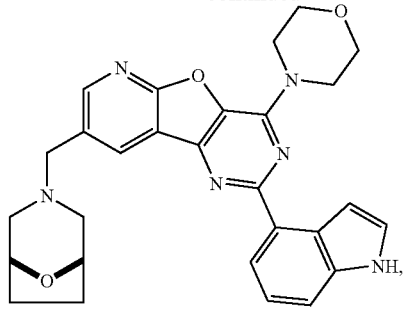

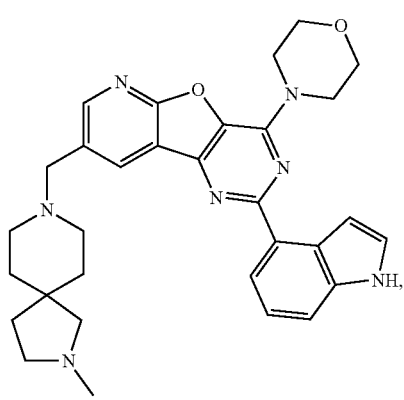

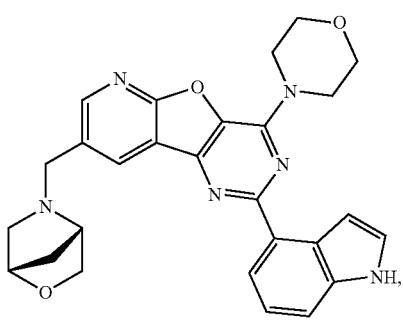

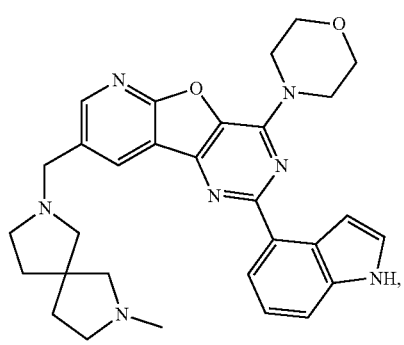

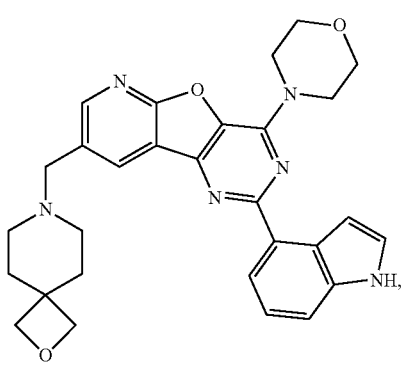

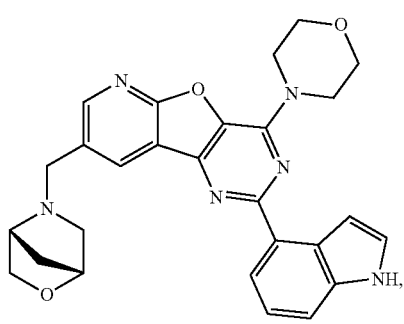

-continued

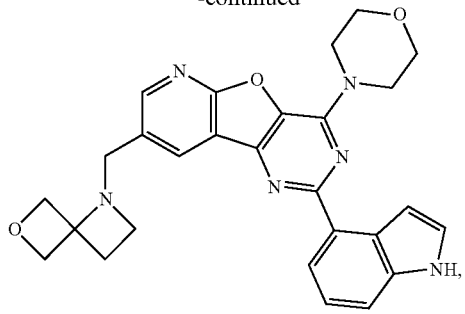

or a pharmaceutically acceptable salt thereof.

15. The method according to claim 14, wherein the compound of formula (I) is:

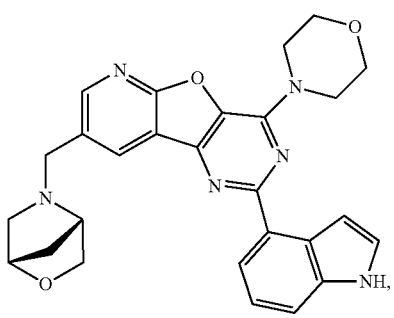 [SMILES: c1cc(-c2nc(N3CCOCC3)c3oc4ncc(CN5C[C@@H]6C[C@H]5CO6)cc4c3n2)c2cc[nH]c2c1]

or a pharmaceutically acceptable salt thereof.

16. A method of treating a cancer selected from the group consisting of chronic myelogenous leukaemia, acute myeloid leukaemia, lymphoma, and solid tumours in a patient in need thereof comprising administering to the patient a therapeutically effective amount of at least one compound and at least one second agent, wherein the compound is

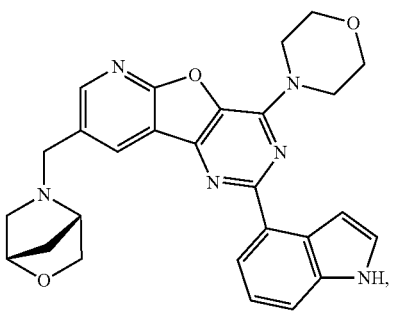 [SMILES: c1cc(-c2nc(N3CCOCC3)c3oc4ncc(CN5C[C@@H]6C[C@H]5CO6)cc4c3n2)c2cc[nH]c2c1]

or a pharmaceutically acceptable salt thereof, and the second agent is ibrutinib.

17. A method of treating a cancer selected from the group consisting of chronic myelogenous leukaemia, acute myeloid leukaemia, lymphoma, and solid tumours in a patient in need thereof comprising administering to the patient a therapeutically effective amount of at least one compound and at least one second agent, wherein the compound is

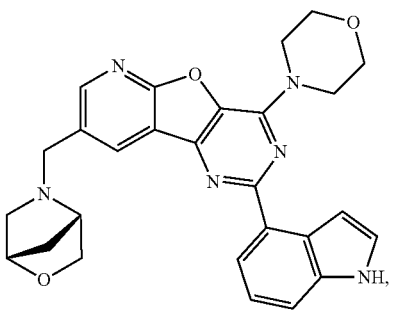 [SMILES: c1cc(-c2nc(N3CCOCC3)c3oc4ncc(CN5C[C@@H]6C[C@H]5CO6)cc4c3n2)c2cc[nH]c2c1]

or a pharmaceutically acceptable salt thereof, and the second agent is selumetinib.

* * * * *